US010299967B2

(12) United States Patent
Schneider et al.

(10) Patent No.: US 10,299,967 B2
(45) Date of Patent: May 28, 2019

(54) METHODS AND APPARATUSES FOR MOVING AND/OR TRANSFERRING MULTIPLE DISCRETE ARTICLES

(71) Applicant: The Procter & Gamble Company, Cincinnati, OH (US)

(72) Inventors: Uwe Schneider, Cincinnati, OH (US); Clifford Theodore Papsdorf, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/953,756

(22) Filed: Apr. 16, 2018

(65) Prior Publication Data

US 2018/0228661 A1    Aug. 16, 2018

Related U.S. Application Data

(63) Continuation of application No. 15/351,469, filed on Nov. 15, 2016, now Pat. No. 9,968,493.

(60) Provisional application No. 62/261,444, filed on Dec. 1, 2015.

(51) Int. Cl.

| B65G 47/52 | (2006.01) |
| B65G 47/00 | (2006.01) |
| B65G 47/32 | (2006.01) |
| A61F 13/15 | (2006.01) |
| B65G 47/244 | (2006.01) |
| B65G 47/84 | (2006.01) |
| B65H 29/24 | (2006.01) |
| B65H 39/14 | (2006.01) |

(52) U.S. Cl.
CPC ...... *A61F 13/15764* (2013.01); *B65G 47/244* (2013.01); *B65G 47/848* (2013.01); *B65H 29/241* (2013.01); *B65H 39/14* (2013.01); *B65H 2301/33216* (2013.01); *B65H 2406/3454* (2013.01); *B65H 2406/363* (2013.01); *B65H 2406/365* (2013.01); *B65H 2406/3632* (2013.01); *B65H 2511/10* (2013.01)

(58) Field of Classification Search
None
See application file for complete search history.

(56) References Cited

U.S. PATENT DOCUMENTS

| 3,491,718 | A | * | 1/1970 | McBride | ............... B05B 12/122 118/685 |
| 4,958,649 | A | | 9/1990 | Petho | |
| 8,607,959 | B2 | | 12/2013 | Papsdorf et al. | |
| 8,720,666 | B2 | | 5/2014 | Papsdorf et al. | |
| 8,820,513 | B2 | | 9/2014 | Papsdorf et al. | |
| 8,833,542 | B2 | | 9/2014 | Papsdorf et al. | |
| 8,944,235 | B2 | | 2/2015 | Papsdorf et al. | |

(Continued)

OTHER PUBLICATIONS

International Search Report and Written Opinion, PCT/US2016/062040, dated Feb. 23, 2017.
All Office Actions, U.S. Appl. No. 15/351,469.

*Primary Examiner* — Kavel Singh
(74) *Attorney, Agent, or Firm* — Christian M. Best; Andrew J. Hagerty

(57) ABSTRACT

Methods and apparatuses for moving and/or transferring discrete articles are described. In particular, the methods and apparatuses relate to flexible arrangements to move and/or transfer discrete articles that vary in size and/or shape with minimal to no change in equipment.

20 Claims, 19 Drawing Sheets

(56) References Cited

U.S. PATENT DOCUMENTS

| | | |
|---|---|---|
| 9,221,621 B2 | 12/2015 | Papsdorf et al. |
| 9,227,794 B2 | 1/2016 | Papsdorf et al. |
| 9,266,684 B2 | 2/2016 | Papsdorf et al. |
| 9,283,121 B1 | 3/2016 | Papsdorf et al. |
| 9,850,404 B2 * | 12/2017 | Hsieh ................. B05C 1/08 |
| 2013/0270069 A1 | 10/2013 | Papsdorf et al. |
| 2014/0109739 A1 | 4/2014 | Schneider |
| 2014/0110052 A1 | 4/2014 | Findley et al. |
| 2016/0074239 A1 | 3/2016 | Papsdorf et al. |

* cited by examiner

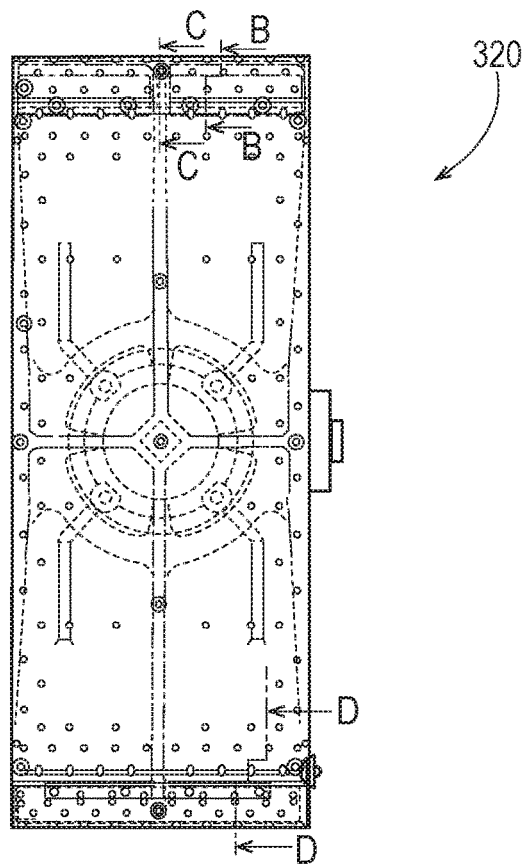
Fig. 10
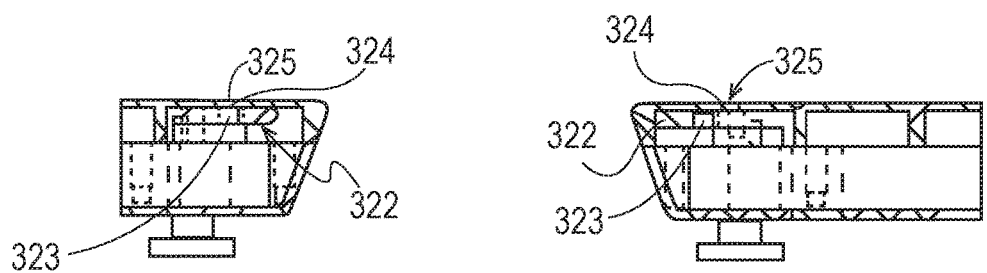
Fig. 11                    Fig. 12

METHODS AND APPARATUSES FOR MOVING AND/OR TRANSFERRING MULTIPLE DISCRETE ARTICLES

CROSS REFERENCE TO RELATED APPLICATIONS

This application is a continuation of, and claims priority under 35 U.S.C. § 120 to, U.S. patent application Ser. No. 15/351,469, filed on Nov. 15, 2016, which claims the benefit, under 35 U.S.C. § 119(e), to U.S. Provisional Patent Application Ser. No. 62/261,444, filed on Dec. 1, 2015, which are both herein incorporated by reference in their entirety.

FIELD OF THE INVENTION

The present disclosure generally relates to methods and apparatuses for transferring multiple discrete articles that vary in size and/or shape.

BACKGROUND OF THE INVENTION

Absorbent articles, such as taped diapers or pant diapers, for example, may be manufactured by a process where discrete articles, such as a chassis of a taped diaper or a pant diaper comprising a topsheet, a backsheet, and an absorbent core, for example, are applied to one or more moving webs of components, such as webs of front and rear belt portions, for example. To achieve this, a transfer assembly may be provided that comprises one or more transfer members and a frame defining a rotation axis. The transfer member(s) may orbit about the rotation axis. Each of the transfer members may comprise a transfer surface that is configured to engage one or more of the discrete articles. The transfer members may pick up the discrete articles at a pick-up location and place the discrete articles at a drop-off location within the orbit. In certain instances, the transfer assembly may rotate the discrete articles about 90 degrees, or other suitable angles, between the pick-up location and the drop-off location about a second rotation axis that is perpendicular, or substantially perpendicular, to the rotation axis. Transfer assemblies that rotate and transfer discrete articles are known in the art as "turn and repitch" units because the units turn the discrete articles and repitch them (i.e., change the spacing or "pitch" between them) between the pick-up location and the drop-off location.

FIG. 1 shows an exemplary turn and repitch unit 10 comprising a plurality of transfer members or heads 12 that are configured to orbit about an axis. The transfer heads 12 and their respective outer surfaces 13 are typically designed to accept an article that has a specific size and shape. To run a different shaped and/or sized article on the same manufacturing line requires the transfer heads to be changed out for different transfer heads specific to the new article. But the time and effort that it would take to change all of the relatively large number of transfer heads generally associated with commercial transfer units can dictate instead changing out the entire operational unit. Entire unit operation change outs can of course lead to increased capital expenditure, maintenance, and manufacturing line downtime.

Accordingly, what is needed are methods and apparatuses for transferring or moving varying sized and/or shaped discrete articles on a single manufacturing line that overcome at least some of the foregoing shortcomings in the art.

While the Background section above highlighted turn and repitch units, the skilled artisan should appreciate that the methods and apparatuses disclosed herein are not limited to such.

SUMMARY OF THE INVENTION

In accordance with one aspect of the present invention, there has now been provided a first method comprising a first step of providing a transfer member comprising a transfer surface that comprises a first zone comprising a first plurality of fluid ports and being configured to accept a first discrete article, and a second zone that substantially surrounds the first zone and that comprises a second plurality of fluid ports, wherein the first zone and the second zone collectively are configured to accept a second discrete article that is different in size and/or shape from the first discrete article. The method comprises a second step of applying fluid pressure only to the first plurality of fluid ports while contacting the first discrete article with the transfer surface. And the method comprises a third step of applying fluid pressure to both the first plurality of fluid ports and the second plurality of fluid ports while contacting the second discrete article with the transfer surface.

In accordance with another aspect of the present invention, there has now been provided a second method comprising a first step of providing a transfer member comprising a fluid pressure chamber comprising a wall that includes an inner surface, an outer surface, a first plurality of fluid ports extending from an inlet on the inner surface to an outlet on the outer surface, and a second plurality of fluid ports extending from an inlet on the inner surface to an outlet on the outer surface. The method comprises a second step of applying fluid pressure to the fluid pressure chamber. The method comprises a third step of communicating fluid pressure to the first plurality of fluid ports while impeding fluid pressure to at least some of the second plurality of fluid ports to hold a first discrete article on the outer surface. The method comprises a fourth step of communicating fluid pressure to both the first plurality of fluid ports and the second plurality of fluid ports to hold a second discrete article on the outer surface, wherein the second discrete article is different in size and/or shape from the first discrete article.

In accordance with yet another aspect of the present invention, there has now been provided a third method comprising a first step of providing a transfer member comprising a fluid pressure chamber comprising a wall that includes an inner surface, an outer surface, a first plurality of fluid ports extending from an inlet on the inner surface to an outlet on the outer surface, and a second plurality of fluid ports extending from an inlet on the inner surface to an outlet on the outer surface. The method comprises a second step of providing a stem that extends from the transfer member and that comprises a first fluid conduit to the fluid pressure chamber and second fluid conduit to the fluid pressure chamber. The method comprises a third step of providing a fluid restrictor associated with the stem, wherein the fluid restrictor is moveable form a first position to a second position. The method comprises a fourth step of communicating fluid pressure the stem. The method comprises a fifth step of positioning the fluid restrictor to the first position so that fluid pressure is communicated only to the first plurality of fluid ports via the first conduit to hold a first discrete article on the outer surface. The method comprises a sixth step of positioning the fluid restrictor in the second position so that fluid pressure is communicated to both the first plurality of fluid ports via the first conduit and the second plurality of fluid ports via the second conduit to hold a second discrete article on the outer surface, wherein the second discrete article is different in size and/or shape from the first discrete article.

BRIEF DESCRIPTION OF THE DRAWINGS

The following detailed description of specific embodiments of the present invention can be best understood when read in conjunction with the drawings enclosed herewith.

FIG. 10 is top view of the transfer member shown in FIG. 8.

FIG. 11 is a cross-sectional view taken through line B-B in FIG. 10.

FIG. 12 is a cross-sectional view taken through line C-C in FIG. 10.

Figure 1:
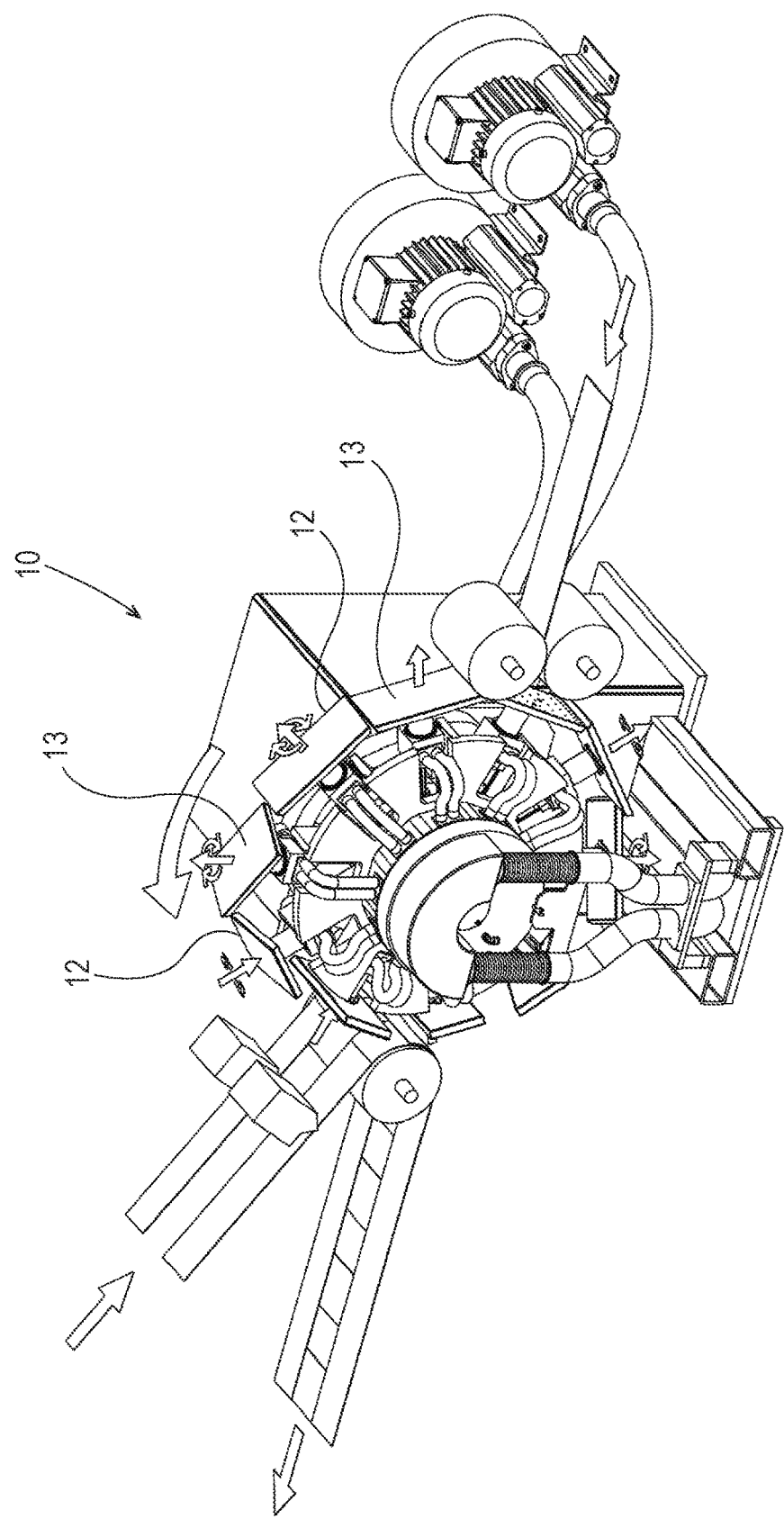
FIG. 1 is a perspective view of a turn and repitch unit.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein the phrase "method for transferring and/or moving multiple different discrete articles" includes manufacturing applications such as turning discrete articles from one orientation to another orientation, moving discrete articles from one location to another location, adjusting spacing of discrete articles (repitching), and combinations thereof. Exemplary applications include servo patch placers, turner units, and turn and repitch units.

As used herein the term "discrete article(s)" refers to absorbent articles, pants, taped diapers, sanitary napkins, bandages, medical pads and dressings, and any other suitable articles, in any industry, capable of being transferred using the transfer apparatuses and methods of the present disclosure. Discrete articles may also refer herein to components or portions of the absorbent articles, pants, taped diapers, sanitary napkins, bandages, medical pads and dressings, and other suitable articles. The discrete articles may be flexible. In one example, discrete articles may refer herein to a chassis of a taped diaper or a pant. The chassis may comprise a topsheet, a backsheet, an optional single or dual layer acquisition system, and an absorbent core disposed between at least a portion of the topsheet and the backsheet. The chassis may also comprise stretched elastic elements such as leg elastics and inner barrier leg cuff elastics, for example.

As used herein, the term "absorbent article(s)" refers to consumer products whose primary function is to absorb and retain bodily exudates and wastes. Absorbent articles as used herein may refer to pants, taped diapers, and/or sanitary napkins (e.g., feminine hygiene products). The term "absorbent articles" also specifically includes adult incontinence products, in any form. Absorbent articles may be disposable, durable, or semi-durable.

As used herein the term "disposable" describes absorbent articles which generally are not intended to be laundered or otherwise restored or reused as an absorbent article (e.g., they are intended to be discarded after a single use and may also be configured to be recycled, composted, or otherwise disposed of in an environmentally compatible manner).

As used herein the term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers in various configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

As used herein the term "pant" refers to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be formed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be formed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

Figure 2:
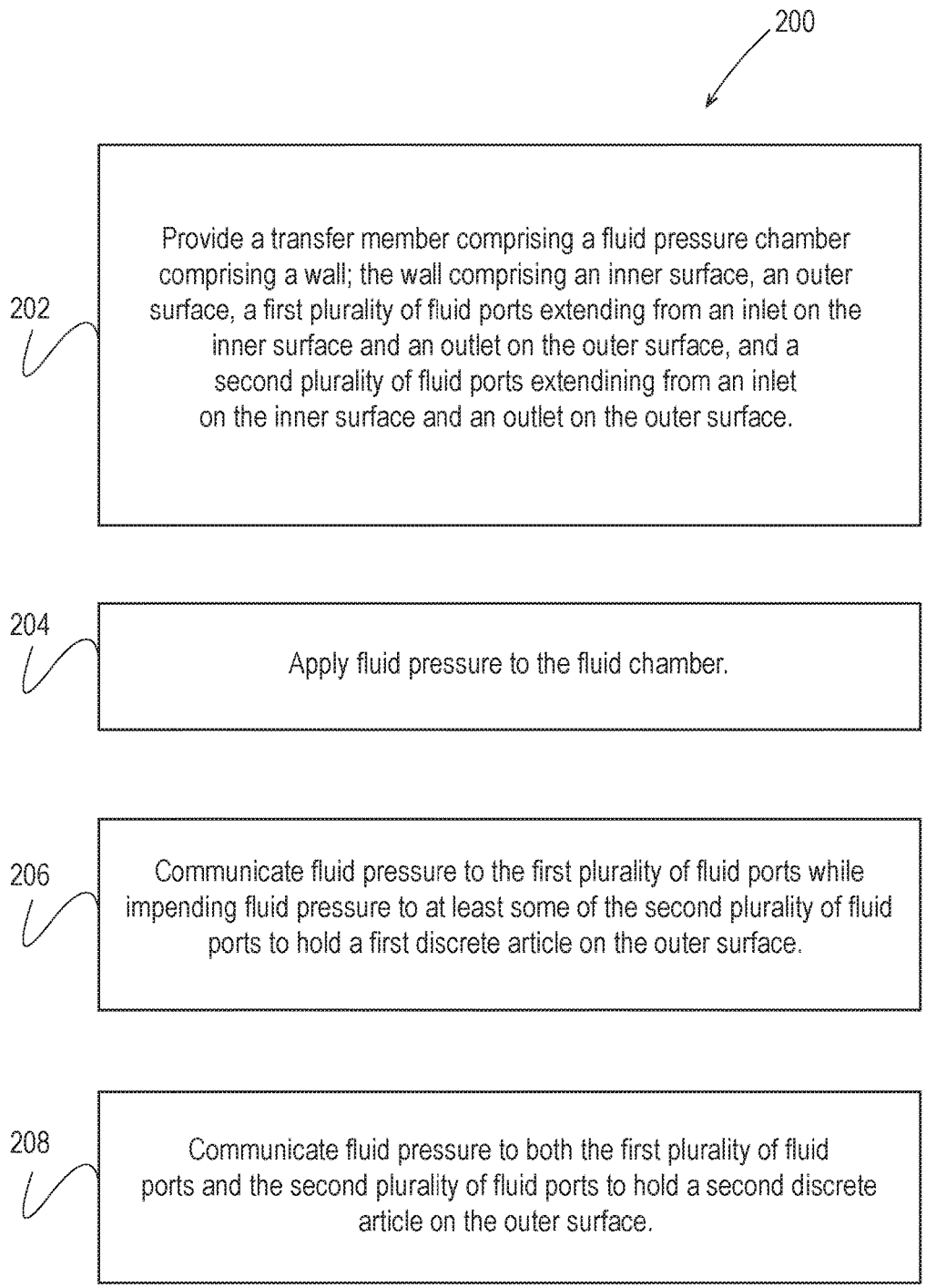
FIG. 2 is a flow chart of one exemplary method described herein.

The present invention is directed to methods and apparatuses for moving and/or transferring discrete articles. In particular, the methods and apparatuses relate to flexible arrangements to move and/or transfer discrete articles that vary in size and shape with minimal to no change in equipment. FIG. 2 includes a flow diagram of one exemplary method 200 that includes four steps. Step 202 includes providing a transfer member comprising a fluid pressure chamber comprising a wall. The wall has an inner surface and an outer surface. A first plurality of fluid ports and a second plurality of fluid ports extend form the inner surface to the outer surface. Step 204 includes applying fluid pressure (e.g., vacuum) to the fluid chamber. Step 206 includes communicating fluid pressure to the first plurality of fluid ports while impeding fluid pressure (e.g., by reducing the level/amount of incoming fluid pressure) to the second plurality of fluid ports to hold a first discrete article on the outer surface of the transfer member. Step 208 includes communicating fluid pressure to both the first plurality of fluid ports and the second plurality of fluid ports to hold a second discrete article on the outer surface of the transfer member, wherein the second discrete article has a different size and/or shape form the first discrete article.

Exemplary method 200 can be performed with numerous different apparatuses, some of which will now be described. FIGS. 3-7 show a transfer member 300 in the form of a transfer head.

Transfer member 300 includes a tray 302 and a cover (wall) 304 that when assembled define an internal pressure chamber. The outer surface 306 of cover 304 includes three zones 306A, 306B, and 306C. A first plurality of fluid ports 308 are disposed in zones 306B, while a second plurality of fluid ports 310 are disposed in zones 306A and 306C. Zone 306B is configured to accept a first discrete article. And zones 306A, 306B, and 306C are collectively configured to accept a second discrete article that is larger than the first discrete article.

Figure 6:
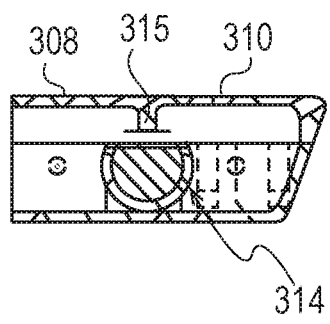
FIG. 6 is a cross-sectional view as taken through line B-B in FIG. 5.
Figure 7:
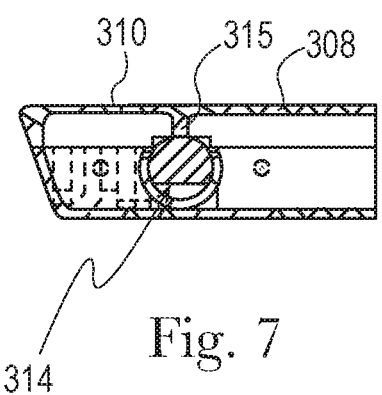
FIG. 7 is a cross-sectional view as taken through line C-C in FIG. 5.
Figure 8:
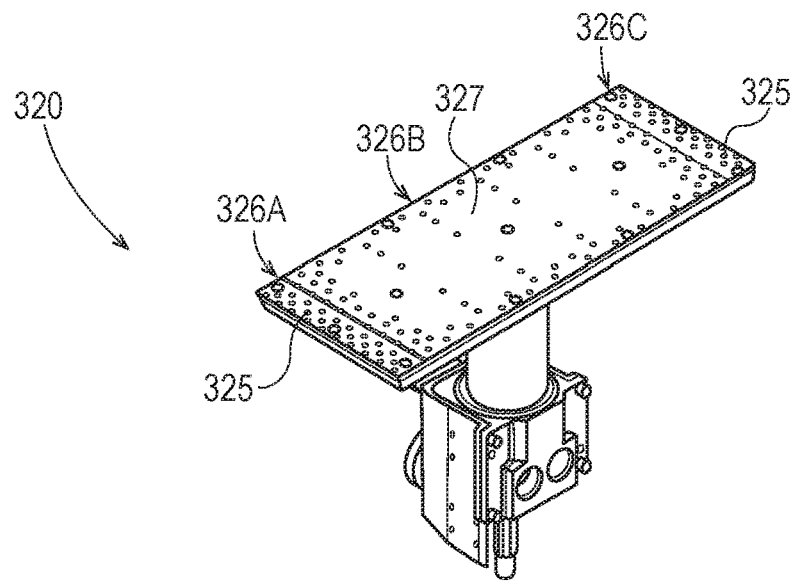
FIG. 8 is a top perspective view of a second exemplary transfer member comprising multiple fluid port zones.

A rotary valve mechanism 312 is disposed within the pressure chamber at the boundary of the zones. A valve rod 314 is employed, which has an asymmetric cross-sectional geometry about its axis of rotation. When the rotary valve mechanism 312 is in a closed position as shown in FIG. 7 (via rod 314 contacting rib 315), fluid pressure is communicated to only the first plurality of fluid ports 308. When the rotary valve mechanism 312 is in an open position as shown in FIG. 6, fluid pressure is communicated to both the first plurality of fluid ports 308 and the second plurality of fluid ports 310.

The outer surface (e.g., outer surface 306) of transfer members as provided herein may be flat, substantially flat, or may comprise one or more flat portions in one or more directions. Substantially flat, as used herein, means the transfer member surface used to support and transport a discrete article conforms to a plane within about 0-10 mm, and alternatively about 0-5 mm, not including fluid ports and bolt holes, as discussed below. Example transfer member outer surfaces are illustrated as rectangular, but it is to be understood that other transfer member outer surfaces may be formed of other suitable shapes, such as squares, circles, or ovals, for example. A portion of each transfer member outer surface may be flat, or substantially flat, while other portions may be arcuate.

The fluid ports (e.g., ports 310) may have any suitable shape, such as elongate slots, circular or ovate openings, and/or rectangular, square, or triangular openings, for example. The fluid ports may also have mesh, screen, or other porous materials extending thereover. The fluid ports may be linear or non-linear, continuous or non-continuous. In a form, a first transfer member may have an outer surface having a first pattern of fluid ports and a second transfer member may have an outer surface having a second pattern of fluid ports. In other instances, the patterns on all of the transfer member outer surfaces may be the same. A positive or a negative (vacuum) fluid pressure may be applied to the fluid ports through various fluid conduits and fluid lines. Some fluid ports, at various times, may not have any fluid pressure being applied thereto. The fluid pressures may initiate in one or more fluid movement members or sources, such as, for example, one or more fluid pumps, vacuum pumps, pressure blowers, or fans. The fluid may be air or other gas, for example. Some fluid ports may be configured to provide a positive pressure, while at the same time, other fluid ports of the same transfer member may be configured to provide a negative pressure or no fluid pressure. In various instances, some of the fluid ports may be configured to provide a first fluid pressure (positive or negative), while at the same time, other fluid ports of the same transfer member may be configured to provide a second fluid pressure (positive or negative). The first fluid pressure may be greater than or less than the second fluid pressure.

Vacuum or negative fluid pressure is communicated to hold a discrete article on the transfer member. For transferring the discrete article off of the transfer member, the vacuum can be discontinued and/or positive fluid pressure can be employed to effectively "blow" the article off of the transfer member.

Figure 3:
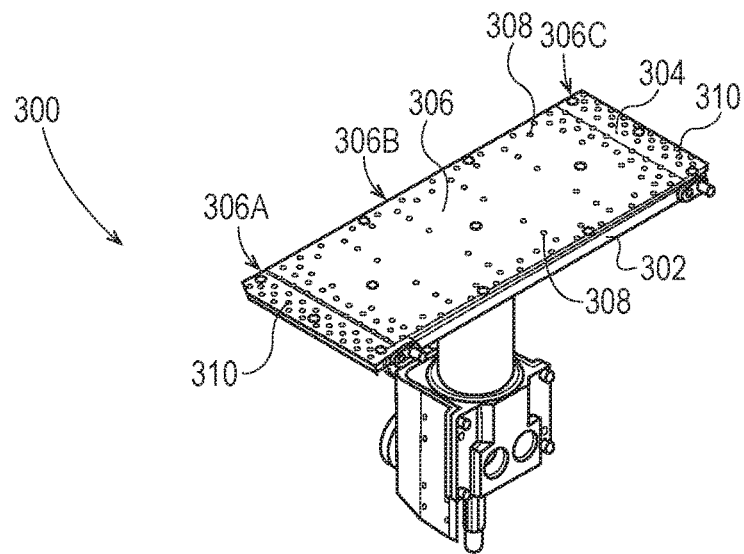
FIG. 3 is a top perspective view of a first exemplary transfer member comprising multiple fluid port zones.
Figure 4:
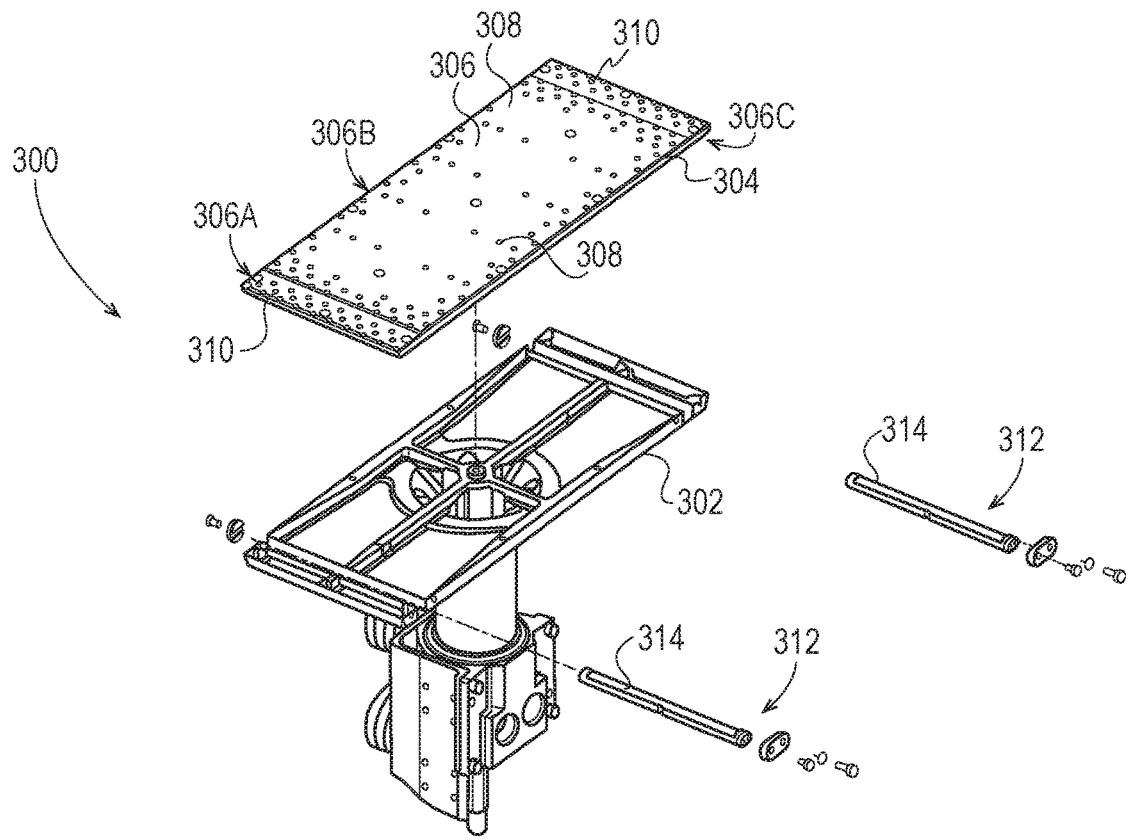
FIG. 4 is an exploded perspective view of the transfer member shown in FIG. 3.
Figure 5:
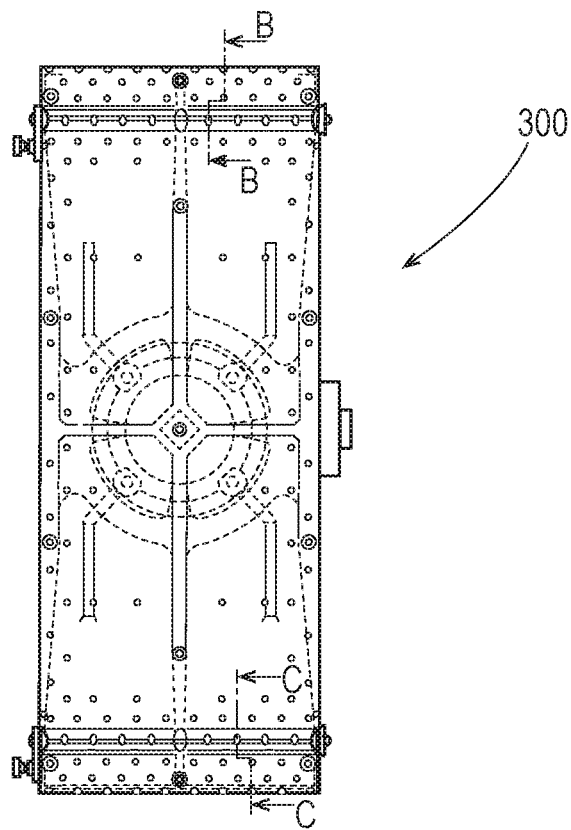
FIG. 5 is a top view of the transfer member shown in FIG. 3.

As shown in FIGS. 3 and 4, a manual mechanism (a spring plunger detent in a pivot link) is employed to rotate the valve 312. A manufacturing line operator pulls the spring plunger and rotates the valve rod 314 to whatever position is needed for accepting a targeted discrete article configuration. Thus, in a matter of a few minutes the transfer members can be adjusted for accepting two differently configured discrete articles. This can address lengthy manufacturing down time associated with changing out complete transfer members or an entire unit operation apparatus ad discussed in the background section above. An automated valve mechanism could alternatively be employed in the overall design approach illustrated in FIGS. 3-7. For example, operation of valve 312 could be automatically operated by internal or external actuators that are controlled by a control system associated with the manufacturing line in which the transfer members are employed. This would enable automated selection between fluid communication with just fluid ports 308 and fluid communication with both fluid ports 308 and fluid ports 310 without the need for a human operator to adjust the valve. Valve 312 can be actuated by a pneumatic actuator, an electric solenoid, a motorized actuator, or any other form of actuator internal to transfer member 320. Valve 312 can also be actuated by cooperation with an actuation mechanism external to transfer member 320. This could include, for example, an electrically or pneumatically actuated control surface that is extended to cooperate with a follower attached to a rocker arm on rotary valve 312. This could also include a robotic arm that adjusts the rotary position of valve 312.

Figure 9:
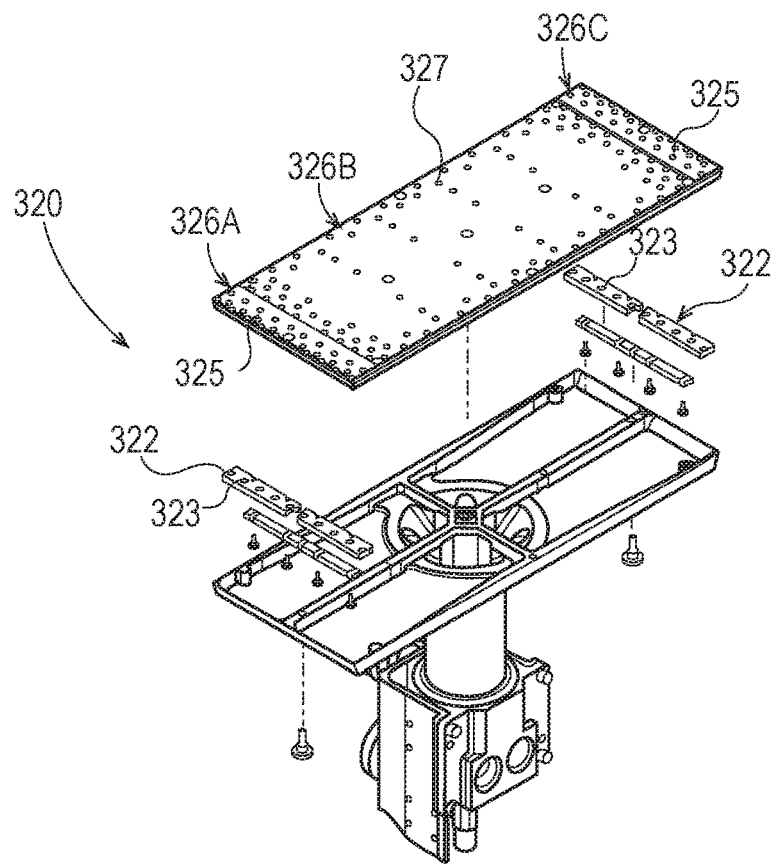
FIG. 9 is an exploded perspective view of the transfer member shown in FIG. 8.

While the approach shown in FIGS. 3-7 employs a rotary valve mechanism, other approaches can be used to impede fluid communication to select groups of fluid ports. For example, and as shown in FIGS. 8-16, fluid ports can be directly covered either internally or externally. Referring to FIGS. 8-12, a transfer member 320 comprising an internal slide gate 322 is illustrated. Slide gate 322 comprises a series of through-holes 323 that can, in a closed position, be out-of-phase or misaligned with inlets 324 associated with a plurality of fluid ports 325 disposed in zones 326A and 326C. Little to no fluid pressure is communicated to the plurality of fluid ports 325 when slide gate 322 is in the closed position. In this arrangement, fluid pressure is communicated to only a plurality of fluid ports 327 disposed in zone 326B to facilitate holding a first discrete article 350 (see FIG. 13) that is configured for just zone 326B. To hold a second discrete article 360 (see FIG. 14) that is larger than the first discrete article 350, slide gate 322 can be moved to an open position whereby through-holes 323 are in phase or aligned with inlets 324 of the fluid ports 325 in zones 326A and 326C, and fluid pressure can be communicated in all three of the zones. As shown in FIG. 9, a manual mechanism (a locking thumb screw and travel slot) is employed to adjust and hold the position of slide gate 322. A manufacturing line operator loosens the thumb screw and the moves slide gage 322 to one side or the other for accepting a targeted discrete article configuration. Thus, in a matter of a few minutes the transfer members can be adjusted for accepting two differently configured discrete articles. Similar to above, an automated valve mechanism could alternatively be employed in the overall design approach illustrate din FIGS. 8-12.

Figure 13:
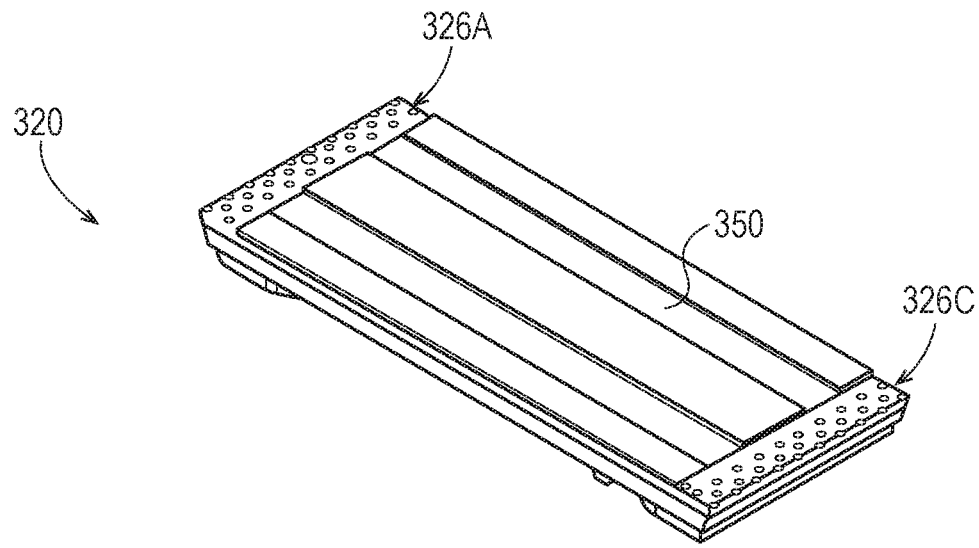
FIG. 13 is a top perspective view of a transfer member holding a first discrete article on its outer surface.
Figure 14:
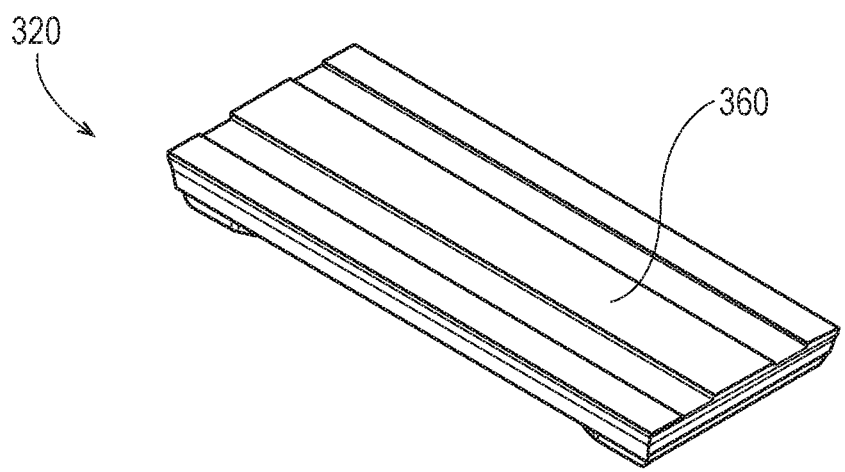
FIG. 14 is a top perspective view of the transfer member shown in FIG. 13 holding a second discrete article on its outer surface.
Figure 15:
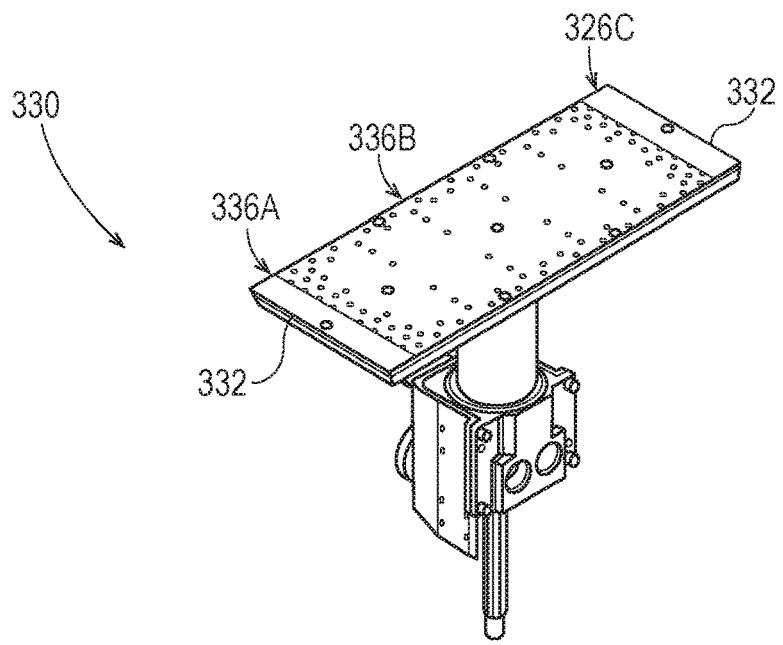
FIG. 15 is a top perspective view of a third exemplary transfer member comprising multiple fluid port zones and external masks.
Figure 16:
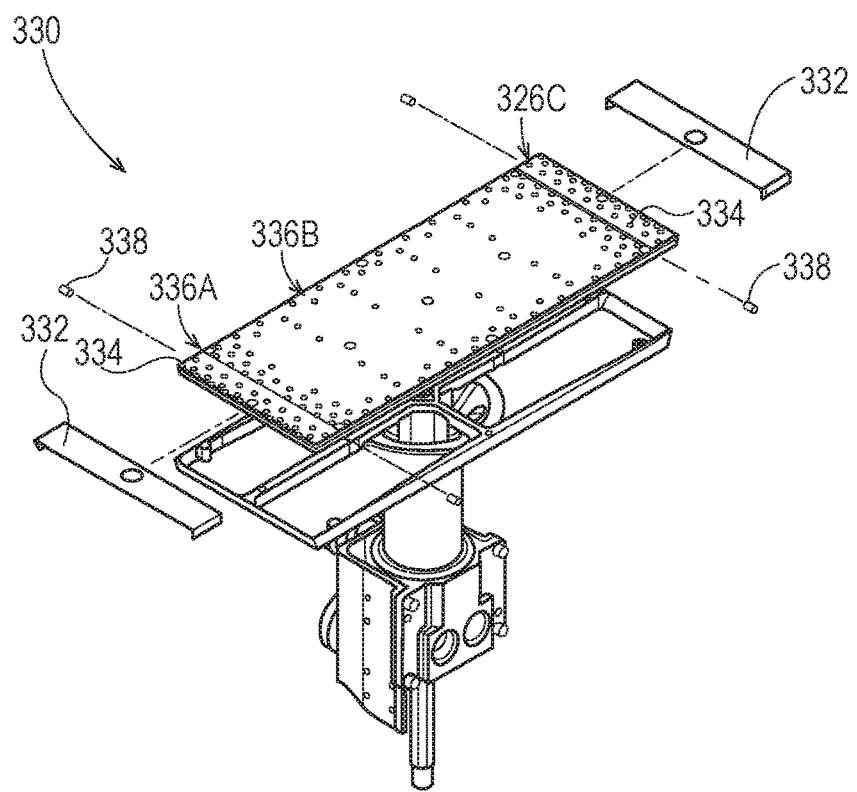
FIG. 16 is an exploded perspective view of the transfer member shown in FIG. 15.

Referring now to FIGS. 15 and 16, a transfer member 330 is shown that is adapted for receiving one or more masks 332 to cover outlets 334 of some of the fluid ports. FIG. 13 shows masks 332 connected to transfer member 330 so that fluid ports disposed in zones 336A and 336C are covered. Transfer member 330, as shown in FIG. 13, is now adapted to receive and hold a first discrete article that fits within zone 336B. If it is desired to hold a second discrete article that is larger than zone 336B, then masks 332 can be removed from transfer member 330, as is shown in FIG. 14. Fluid ports in all of zones 336A, 336B, and 336C are available for acting on the second discrete article. Various affixments can be used to attach covers to the transfer members, such as, for example, spring-loaded detent pins 338.

Figure 17:
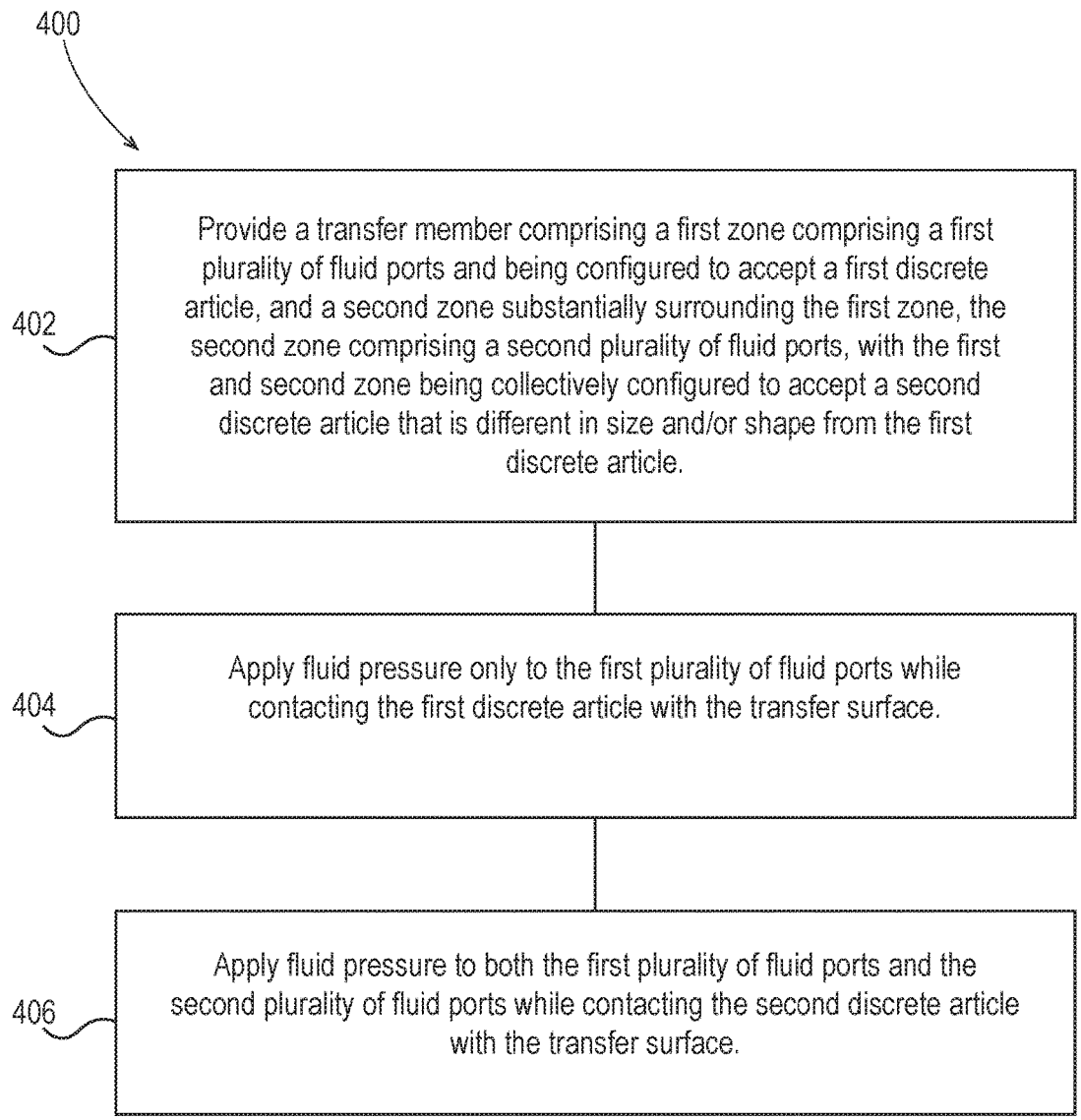
FIG. 17 is a flow chart of another exemplary method described herein.

FIG. 17 includes a flow diagram of another exemplary method 400 according to the present invention that includes three steps. Step 402 includes providing a transfer member comprising a transfer surface that has a first zone that includes a plurality of fluid ports and that is configured to accept a first discrete article, and a second zone that substantially surrounds the first zone and that also includes a plurality of fluid ports. Collectively the first zone and second zone are configured to accept a second discrete article that has a size and/or shape that is different than the first discrete article. Step 404 includes applying fluid pressure only to the plurality of fluid ports in the first zone to hold and/or transfer the first discrete article. And step 406 includes applying fluid pressure to both the first zone and the second zone to hold and/or transfer the second discrete article.

Figure 18:
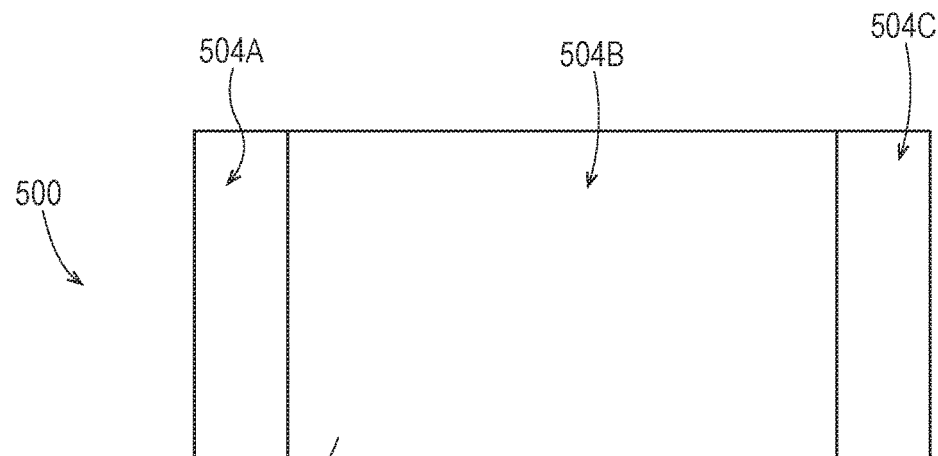
FIG. 18 is a top schematic of a transfer member comprising multiple article holding zones.
Figure 19:
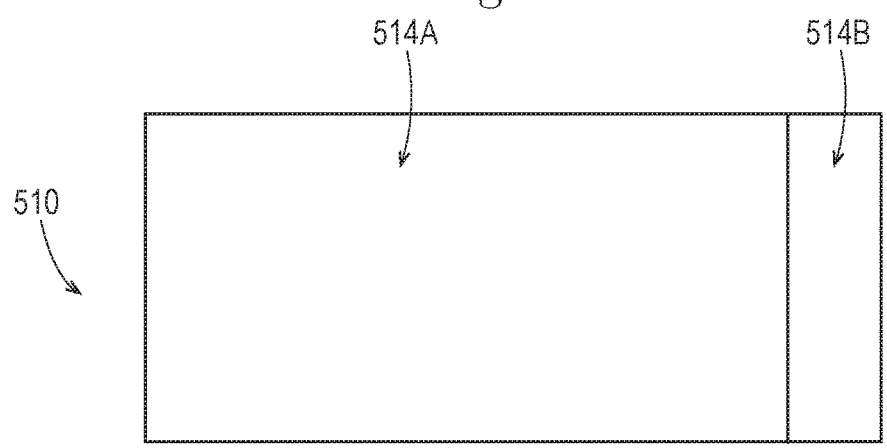
FIG. 19 is a top schematic of a transfer member comprising two article holding zones.
Figure 20:
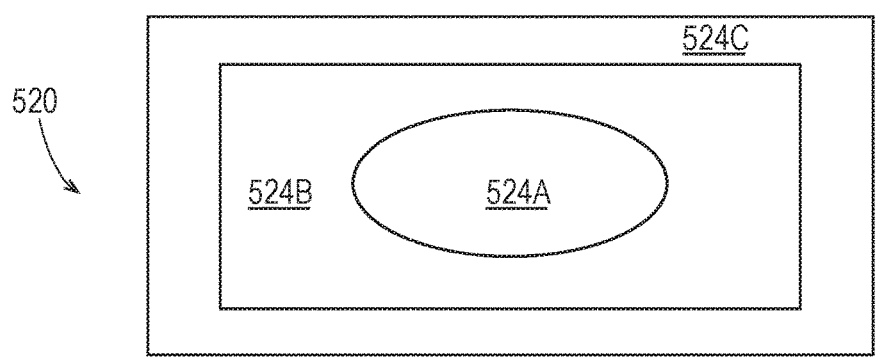
FIG. 20 is a top schematic of a transfer member comprising three concentric article holding zones.

FIGS. 18-20 are simple schematics intended to illustrate that the various zones of a transfer member can be take on a variety of different sizes and shapes, and relative positioning with respect to one another. The figures do not show the fluid ports that would be included in the various zones. FIG. 18 includes a schematic version of the transfer members described above, wherein transfer member 500 includes a surface 502, a first zone 504A, a second zone 504B, and a third zone 504C. Zone 504B can be employed to hold and transfer a first article. To hold and transfer a larger article, zones 504A and/or 504C can be employed in conjunction with zone 504B. FIG. 19 illustrates a transfer member 510 variation that includes only two zones 514A and 514B. FIG. 20 shows a transfer member 520 that includes zones 524A, 524B, and 524C. The zones are arranged in a radial fashion instead of the end-to-end configuration that is shown in FIGS. 18 and 19. FIGS. 18-20 illustrate that the zones can be sized differently, shaped differently, and positioned in a variety of positional relationships.

Figure 21:
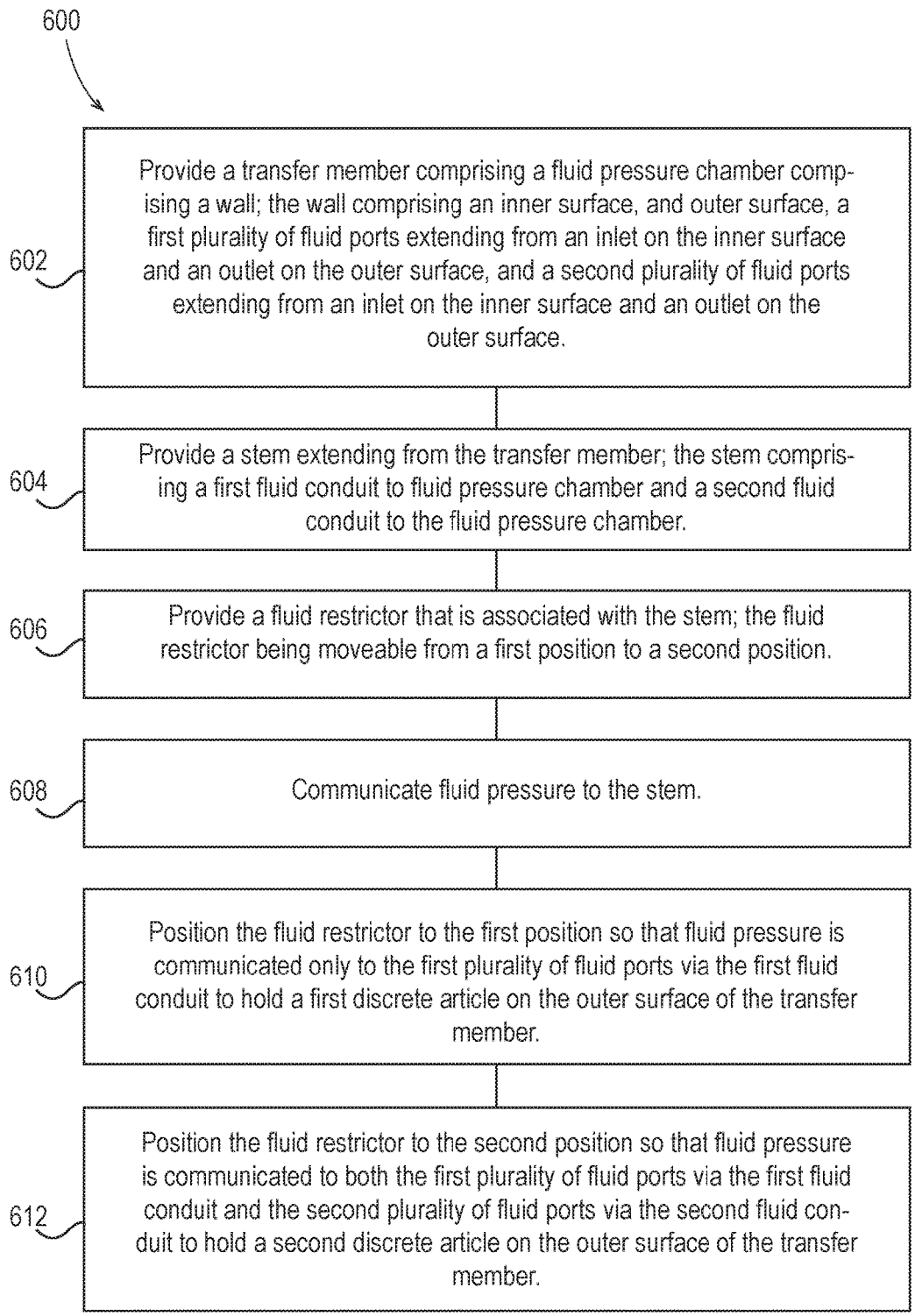
FIG. 21 is a flow chart of yet another exemplary method described herein.

A flow diagram of yet another exemplary method 600 is shown in FIG. 21. Step 602 includes providing a transfer member comprising a fluid pressure chamber comprising a wall. The wall has an inner surface and an outer surface. A first plurality of fluid ports and a second plurality of fluid ports extend from the inner surface to the outer surface. Step 604 includes providing a stem that extends from the transfer member and that includes a first fluid conduit and a second fluid conduit that is in fluid communication with the fluid pressure chamber. Step 606 includes providing a fluid restrictor that is associated with (e.g., disposed within, around, about) the stem, wherein the fluid restrictor is moveable from a first position to a second position. Fluid pressure is communicated to the stem in step 608. Step 610 includes positioning the fluid restrictor to the first position so that fluid pressure is communicated only to the first plurality of fluid ports via the first fluid conduit to hold a first discrete article on the outer surface of the transfer member. And step 612 includes positioning the fluid restrictor to the second position so that fluid pressure is communicated to both the first plurality of fluid ports via the first fluid conduit and the second plurality of fluid ports via the second fluid conduit to hold a second discrete article on the outer surface of the transfer member.

Figure 22:
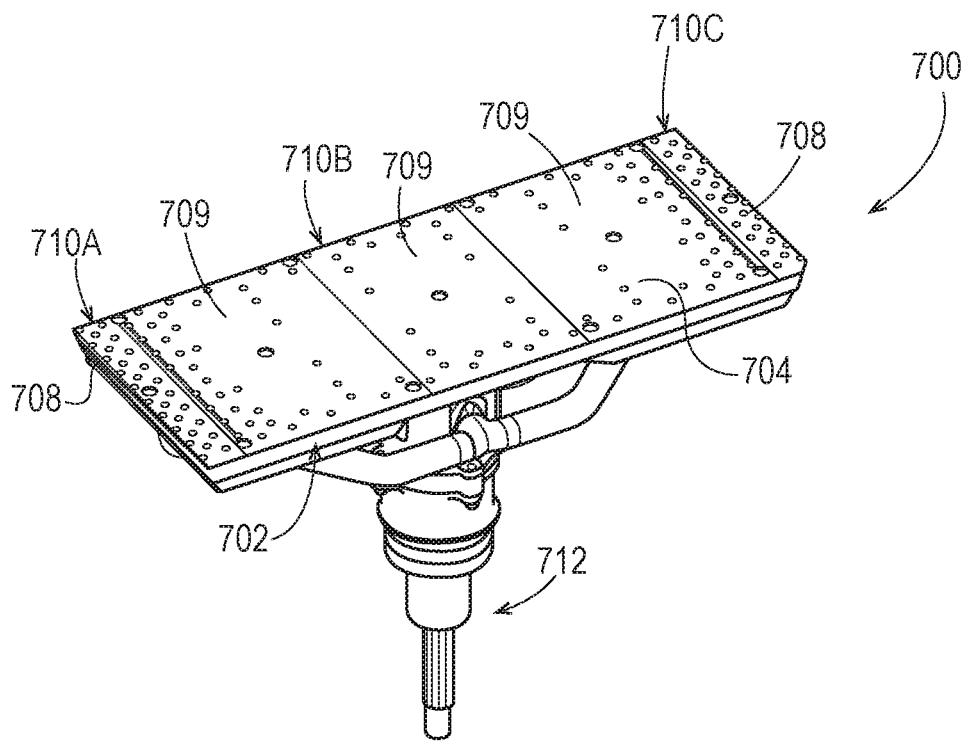
FIG. 22 is a top perspective view of a third exemplary transfer member comprising multiple fluid port zones.
Figure 23:
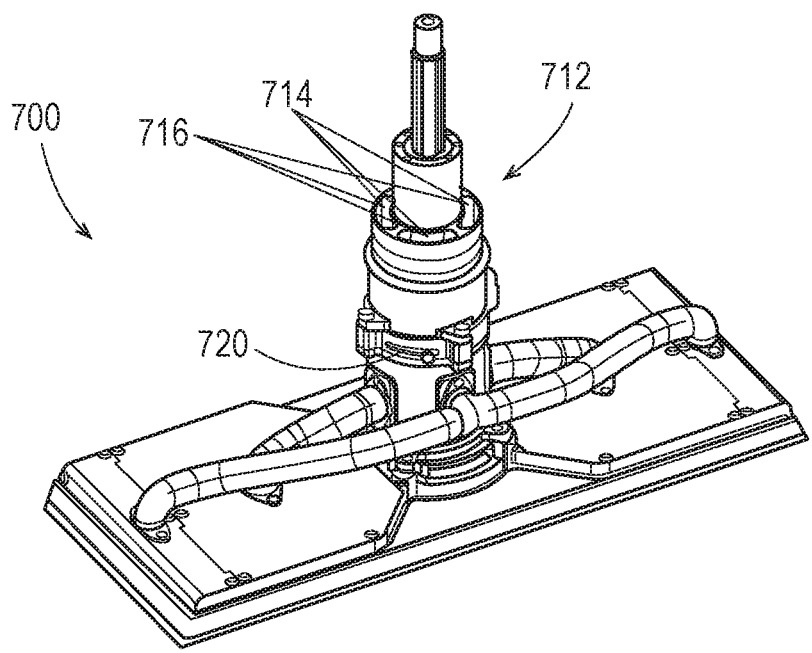
FIG. 23 is a bottom perspective view of the transfer member shown in FIG. 22.
Figure 24:
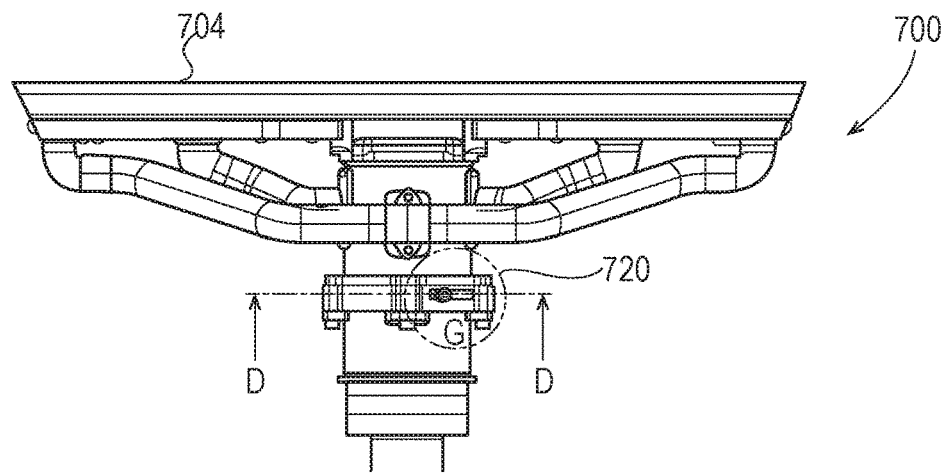
FIG. 24 is an elevation view of the transfer member shown in FIG. 22.
Figure 25:
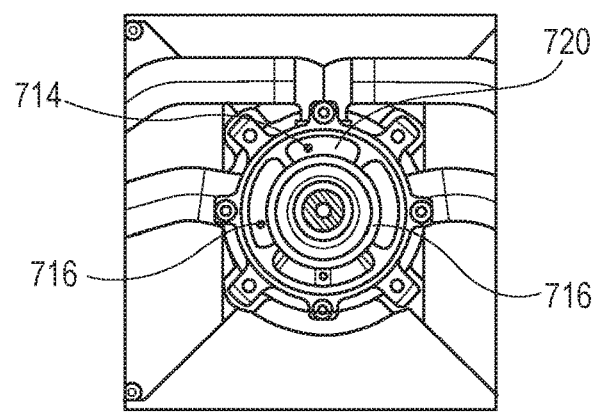
FIG. 25 is a cross-sectional view of a fluid restrictor, associated with the transfer member shown in FIG. 22, in a first position.
Figure 26:
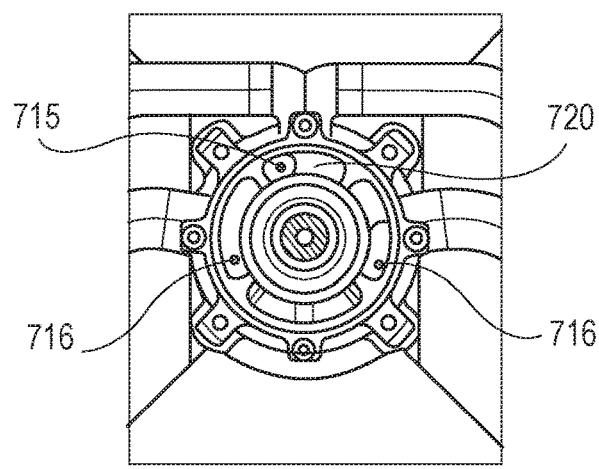
FIG. 26 is a cross-sectional view of a fluid restrictor, associated with the transfer member shown in FIG. 22, in a second position.
Figure 27:
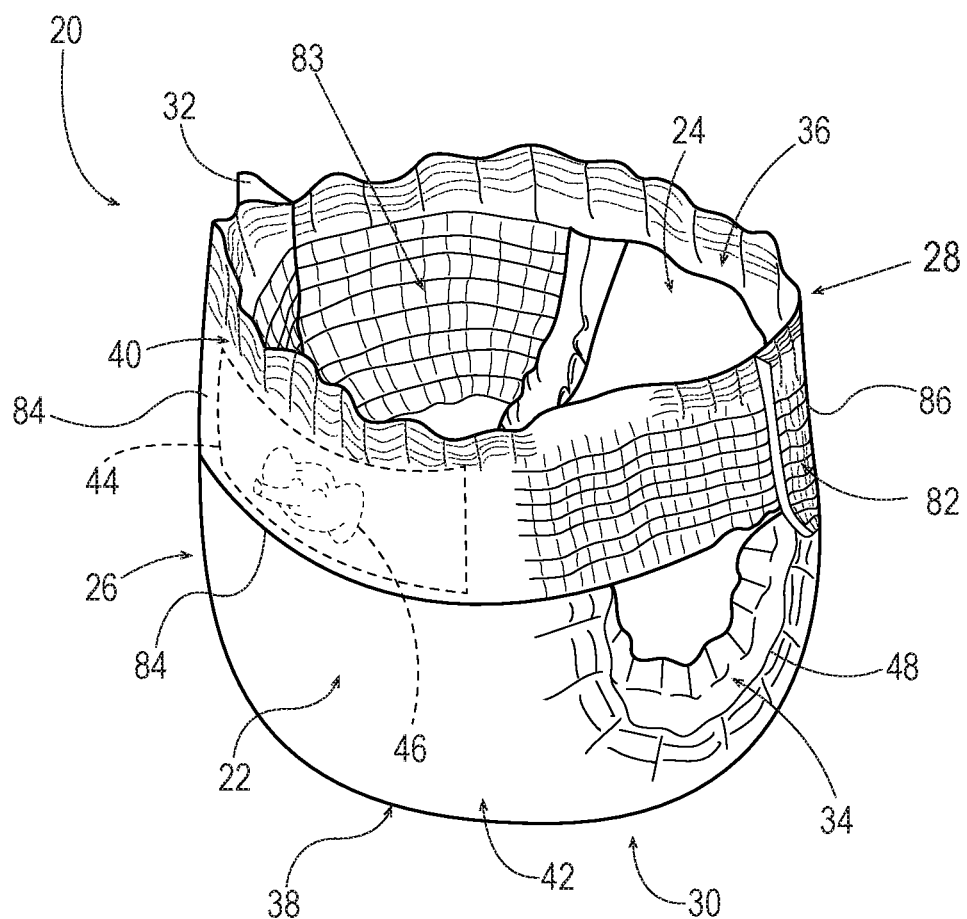
FIG. 27 is a perspective view of an exemplary absorbent article in the form of a pant.

Exemplary method 600 can be performed with numerous different apparatuses and approaches, one of which is described with reference to FIGS. 22-26. FIGS. 22-24 show an exemplary transfer member 700 that includes a pressure chamber 702 having an outer surface 704 (wall) that is configured for receiving, holding, and transferring two different discrete articles. Transfer member 700 includes three zones of fluid ports. Zones 710A and 710C comprise fluid ports 708, and zone 710B comprises fluid ports 709. Fluid ports 709 can be active and fluid ports 708 inactive when a first discrete article is processed. And then both fluid ports 708 and 709 can be active to process a second discrete article that is larger than the first discrete article. A stem 712 extends from transfer member 700. Stems can facilitate a number of different functions: attachment points of transfer members to a rotating drum or other member, reciprocating movement, rotational movement, and/or fluid pressure communication. Stem 712 includes a first fluid conduit 714 and a second fluid conduit 716 for communicating fluid pressure to the fluid ports in zones 710A, 710B, and 710C. Stem 712 also includes a fluid restrictor 720 in the form of a rotary valve member. Fluid restrictor 720 can be placed in a first closed position, as shown in FIG. 26, wherein fluid pressure is only communicated to fluid ports 709 in zone 710B because the fluid pressure in fluid conduit 714 is inhibited/blocked. Fluid restrictor 720 can also be placed in a second open position, as shown in FIG. 27, wherein fluid is allowed to travel through both fluid conduit 714 (via opening 715 in restrictor 720) and fluid conduit 716 so that fluid pressure is communicated to fluid ports 708 and fluid ports 709.

The present disclosure provides, in part, transfer assemblies and transfer members associated with the transfer assemblies for transferring discrete articles and/or flexible discrete articles, such as a chassis of a pant or a taped diaper, for example. The present disclosure also provides, in part, methods for transferring the discrete articles. A chassis of a pant or a taped diaper, for example, may be traveling at a first speed on a first moving carrier member and may be transferred by the transfer members, or portions thereof, of the transfer assemblies to a second moving carrier member traveling at a second speed or at the same speed. The discrete articles may be transferred onto the second moving carrier member to change the speed and/or pitch of the discrete articles and/or to turn the discrete articles, for example. In other embodiments, components, such as webs of front and rear belts or discrete front and rear belts, either of which are configured to together form a portion of a belt in a pant, for example, may be moving over the second moving carrier member. The second moving carrier member may have a first portion carrying the web of front belts and a second portion carrying a web of rear belts. In other embodiments, the second carrier member may comprise two separate moving carrier members; one carrying the web of front belts and the other carrying the web of rear belts. If webs of front and rear belts are provided on the second moving carrier member, the chassis may be transferred from the first moving carrier member to the second moving carrier member and turned so as to apply the waist regions of the chassis to the first and second webs of front and rear belts. A first waist region of the chassis may be applied to the web of first belts and a second waist region of the chassis may be applied to the web of second belts to form an absorbent article that can be formed into a pant or a taped diaper, for example. The waist regions of the chassis may be glued to the webs of belts or otherwise attached to the webs of belts. Further details regarding this example transfer are provided herein.

The transfer assemblies and portions of transfer members of the present disclosure may be able to turn the discrete articles intermediate the first moving carrier member and the second moving carrier member for placement onto one or more webs of components or discrete components traveling over the second moving carrier member or onto the second moving carrier member without being placed on discrete components. In one example, a portion of a transfer member of a transfer assembly may receive a discrete article, such as a taped diaper or pant chassis, for example, from a first moving carrier member and turn it between a first position and a second position (e.g., a 90 degree turn to the discrete article) and apply the discrete article onto webs of front and rear belts traveling on the second moving carrier member to form an absorbent article that can be formed into a taped diaper or a pant. The transfer assemblies and transfer members, or portions thereof, may also be configured to repitch the discrete articles between the first moving carrier member and the second moving carrier member. This "repitching" is changing the spacing between midpoints of the discrete articles relative to each other. In one embodiment, the pitch may be smaller or larger once deposited onto the second moving carrier member compared to when the discrete articles were situated on the first moving carrier member. In other embodiments, the pitch of the discrete articles may not be changed between the first moving carrier member and the second moving carrier member. In various embodiments, the transfer assemblies and portions of the transfer members of the present disclosure may not turn the discrete articles between the first and second moving carrier members, although they may have the ability to do so. In other embodiments, the transfer assemblies and/or transfer members, or portions thereof, may not have the ability to turn the discrete articles during a transfer between the first and second moving carrier members.

It is to be appreciated that the methods and apparatuses of the present disclosure may also be suitable for any other uses that require transfer of a discrete article or a discrete component from a first moving carrier member to a second moving carrier member regardless of the speed of the first and second moving carrier members and regardless of whether the discrete articles or discrete components need to be turned and/or repitched. These other uses may comprise various manufacturing processes for any product, or intermediate product, in any industry.

Figure 28:
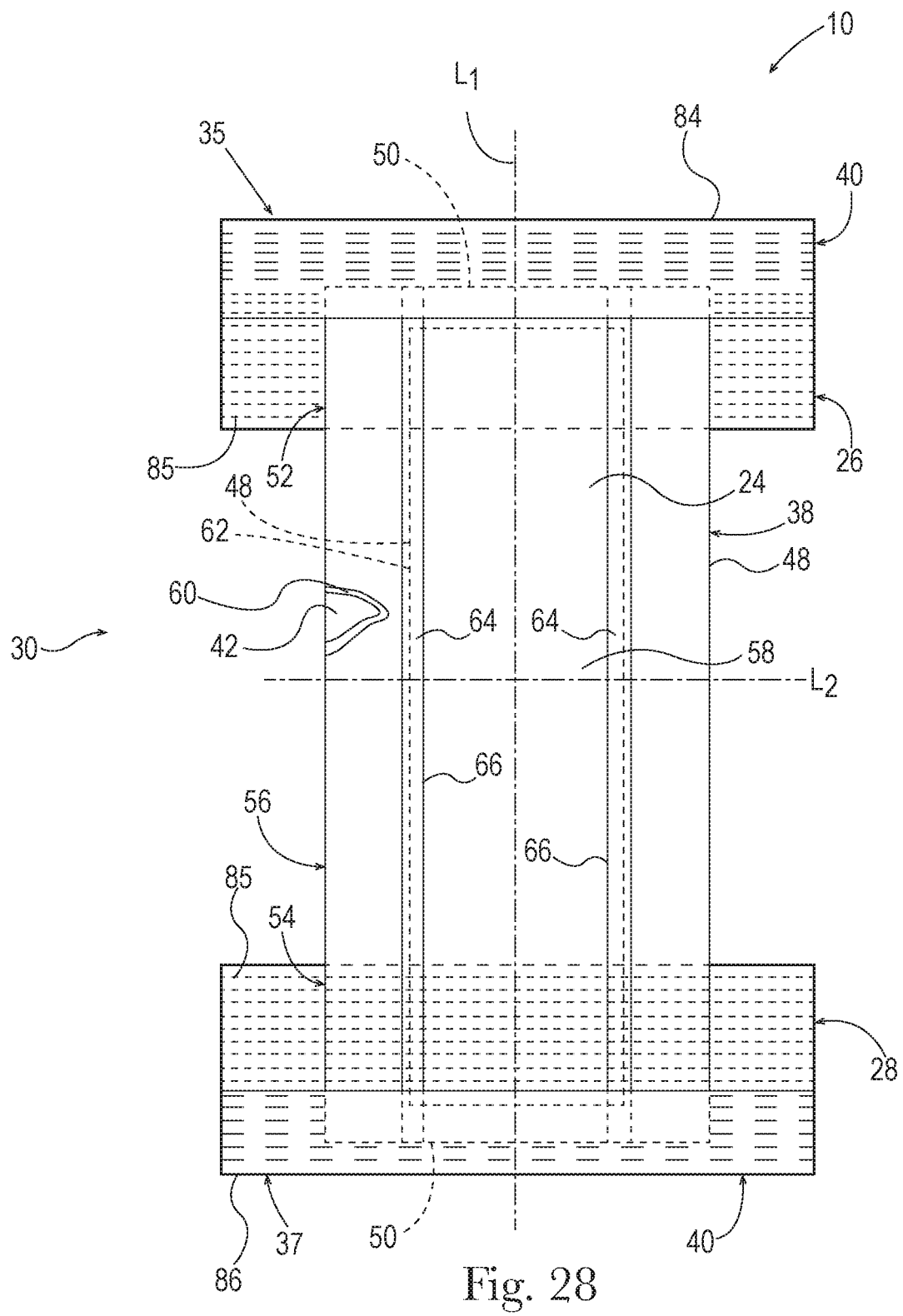
FIG. 28 is a plan view of the pant in FIG. 27 before it is fully assembled.

FIG. 27 illustrates an example of a pant 20 that may be at least partially formed or manufactured using the transfer assemblies and transfer members of the present disclosure. FIG. 28 illustrates an absorbent article 10 that can be formed into the pant 20 of FIG. 27. Those of skill in the art will recognize that FIGS. 27 and 28 are merely examples of one product that may be formed, or at least partially manufactured, using the transfer assemblies and transfer members of the present disclosure. Many other products, including other absorbent articles, pants, or portions thereof, may be formed, or at least partially manufactured, using the transfer assemblies and transfer members of the present disclosure. The absorbent article 10 has a longitudinal central axis L1 and a lateral central axis L2 (see FIG. 28). The pant 20 has an outer surface 22, an inner surface 24 opposed to the outer surface 22, a front waist region 26, a rear waist region 28, a crotch region 30, and seams 32 which join the front waist region 26 and the rear waist region 28 to form two leg openings 34 and a waist opening 36. The seams 32 may be permanent or refastenable. When referring to "pant 20" herein, it will be understood that the absorbent article 10, although not yet formed into the pant 20, may be considered a "pant". It will be understood that the pant 20 is disclosed as an example, but that a taped diaper may also be formed from the absorbent article 10 merely by adding fastening elements and/or landing zones to one or both of the front and rear belts 84 and 86.

Referring to FIGS. 27 and 28, the pant 20 may comprise an absorbent chassis 38 to cover a crotch region of a wearer and a belt 40 extending transversely about the waist opening 36. The pant 20 may also optionally comprise an outer cover layer 42 to cover the chassis 38. The belt 40 may define the waist opening 36 in the pant 20. The belt 40, the chassis 38, and/or the outer cover layer 42 may jointly define the leg openings 34. In one embodiment, the pant 20 may have a patch sheet 44 printed with a graphic 46 thereon, which may be disposed in the front waist region 26, the rear waist region 28, or any other suitable portion of the pant 20. The belt 40 may be formed from a front belt 84 in the front waist region 26 and a rear belt 86 in the rear waist region 28. The front belt 84 may form a front waist edge 35 in the front waist region 26 and the rear belt 86 may form a rear waist edge 37 in the rear waist region 28. The front and rear waist edges 35 and 37 may be laterally opposed about the lateral central axis L2. The belt 40 may form a portion of an outer surface 22 or an inner surface 24 of the pant 20. In other embodiments, the belt 40, or portions thereof, may be disposed intermediate other layers of the chassis 38, such as a topsheet and a backsheet, for example.

The absorbent chassis 38 may absorb and contain body exudates or wastes disposed on the chassis 38. Referring to FIG. 28, the chassis 38 may have a generally rectangular shape having left and right longitudinally extending side edges 48 (hereinafter may be referred to as "longitudinal side edge") and front and rear laterally extending end edges 50 (hereinafter may be referred to as "lateral end edge"). The chassis 38 may also comprise waist panels (i.e., a front waist panel 52 positioned in the front waist region 26 and a rear waist panel 54 positioned in the rear waist region 28) and a crotch panel 56 in the crotch region 30 between the front and rear waist panels 52, 54.

Referring to FIG. 28, the pant 20 may comprise front and rear belts 84 and 86 intended to encircle at least a portion of the waist of the wearer. The front and rear belts 84 and 86 together form at least a portion of, or all of, the belt 40 when joined. The front and rear belts 84 and 86 may be connected by the chassis 38 forming the crotch region 30 of the pant 20. The front and rear belts 84 and 86 may each be formed from a first belt layer 82 possibly forming a portion of the outer surface 22 of the pant 20 and a second belt layer 83 possibly forming a portion of the inner surface 24 of the pant 20. The first and second belt layers 82 and 83 may be comprised of any known materials. Various suitable materials may comprise films, plastic films, apertured plastic films, woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers, stretchable nonwovens, or coated woven or nonwoven webs. The belt 40 may comprise an inner hydrophobic, nonwoven material and an outer hydrophobic, nonwoven material. The front and rear belts 84 and 86 may also comprise a plurality of elastic elements 85 disposed at least partially between the first and second belt layers 82 and 83 thereof and attached to at least one of the first and second belt layers 82 and 83 using adhesives or bonding, for example. The elastic elements 85 may comprise one or more elastic strands, elastic materials, elastomeric films, elastomeric ribbons, elastomeric nonwovens, elastomeric filaments, elastomeric adhesives, elastomeric foams, scrims, or combinations thereof The chassis 38 of the pant 20 may comprise a portion of the outer surface 22, a backsheet 60, a portion of the inner surface 24, a topsheet 58, and an absorbent core 62 disposed between at least a portion of the topsheet 58 and the backsheet 60. In addition, the chassis 38 may comprise elasticized barrier leg cuffs 64 disposed at or adjacent the side edges 48 of the chassis 38. The barrier leg cuffs 64 may provide improved containment of liquids and other body exudates or wastes in the crotch region 30 and may comprise a single layer of material which may be folded to form a barrier leg cuff having two layers. The barrier leg cuffs 64 may extend from the side of the chassis 38 at or adjacent the longitudinal side edge 48 toward the longitudinal central axis L1. The barrier leg cuffs 64 may be folded along the folding lines 66 back toward the longitudinal side edges 48. The front and rear belts 84 and 86 may overlap at least a portion of the chassis 38 and one or both of the front and rear belts 84 and 86 may be disposed on the outer surface 22 of the chassis 38, on the inner surface 24 of the chassis 38, or disposed intermediate various portions of the chassis 38.

In one embodiment, a portion of, or the whole of, the chassis 38 may be made extensible to a degree greater than the inherent extensibility of the material or materials from which the chassis 38 is made, e.g., the backsheet 60. The additional extensibility may be desirable in order to allow the chassis 38 to conform to the body of a wearer during movement by the wearer and or to provide adequate body coverage. The additional extensibility may also be desirable, for example, in order to allow the user of a pant including the chassis 38 having a particular size before extension to extend the front waist region 26, the rear waist region 28, or both of the waist regions of the chassis 38 to provide additional body coverage for wearers of differing size, i.e., to tailor the pant to the individual wearer. Such extension of the waist region or regions may give the chassis 38 a generally hourglass shape, so long as the crotch region 30 is extended to a relatively lesser degree than the waist region or regions, and may impart a tailored appearance to the pant 20 when it is donned or worn. In addition, the additional extensibility may be desirable in order to minimize the cost of the pant 20. For example, an amount of material that would otherwise be sufficient only to make a relatively smaller pant lacking this extensibility may be used to make an article capable of being extended to adequately cover a wearer that is larger than the unextended smaller pant would fit.

A portion of the chassis 38, for example, a portion of the chassis 38 in one or both of the waist regions 26 and 28 may be made laterally extensible to a maximum extensibility greater than a maximum extensibility of another portion of the chassis 38 in the crotch region 30 such that a lateral extension of each of the portions to its maximum extensibility imparts an hourglass shape to the chassis 38. In one embodiment, the portion of the chassis 38 underlying, overlying, and/or immediately adjacent one or both of the front and rear extensible belts 84 and 86 may be made laterally extensible to a maximum extensibility greater than a maximum extensibility of another portion of the chassis 38, for example the crotch region 30, such that a lateral extension of each of the portions to its maximum extensibility facilitates application of the pant 20 onto the body of a wearer by enabling the waist regions 26 and 28 to be extended to fit over the wearer's hips and in addition, opening and orienting the leg openings enabling the wearer to place the legs through the leg openings more effectively.

In one embodiment, the liquid pervious topsheet 58 may be positioned adjacent the body-facing surface of the absorbent core 62 and may be joined thereto and/or to the backsheet 60 by any attachment means known to those of skill in the art. The liquid impervious backsheet 60 may generally be that portion of the pant 20 positioned adjacent the garment-facing surface of the absorbent core 62 and may prevent, or at least inhibit, the bodily exudates and wastes absorbed and contained in the absorbent core 62 from soiling garments that may contact the outer surface 22 of the pant 20.

The topsheet 58, the backsheet 60, and the absorbent core 62 may be manufactured of any known materials. Suitable topsheet materials may comprise porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the pant 20 while still preventing, or at least inhibiting, bodily exudates or wastes from passing through the backsheet 60. Such materials may include nonwoven materials, woven materials, films, and/or laminates comprising a combination of one or more of these materials. In one embodiment, the backsheet 60 may be a film and nonwoven laminate, wherein the nonwoven of the laminate forms the outer cover layer 42.

A suitable absorbent core 62 for use in the pant 20 may comprise any absorbent material which is generally compressible, conformable, non-irritating to the wearer's skin, and capable of absorbing and retaining liquids such as urine and other certain body exudates. In addition, the configuration and construction of the absorbent core 62 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core 62 may comprise a fluid acquisition component, a fluid distribution component, and/ or a fluid storage component. An example of a suitable absorbent core having a fluid acquisition component, a fluid distribution component, and a fluid storage component is described in U.S. Pat. No. 6,590,136.

In one embodiment, the outer cover layer 42 may be disposed on the outer surface 22 of the pant 20 and may cover the crotch panel 56 of the absorbent chassis 38. The outer cover layer 42 may extend into and cover the front waist panel 52 and the rear waist panel 54 of the chassis 38. The outer cover layer 42 may form a portion of the backsheet 60 and/or the chassis 38. In one embodiment, the outer cover layer 42 may be directly joined to and cover a portion of, or all of, the liquid impervious backsheet 60 of the chassis 38. In various embodiments, the outer cover layer 42 may be disposed between the front and rear belts 84 and 86.

The outer cover layer 42 may comprise a material separate from the first and second belt layers 82 and 83 forming the belts 84 and 86. The outer cover layer 42 may comprise two or more layers of materials of any known materials including the materials used for the first and second belt layers 82 and 83. In one embodiment, the outer cover layer 42 may comprise a single layer of a nonwoven web of synthetic fibers. In various embodiments, the outer cover layer 42 may comprise a single layer of hydrophobic, non-stretchable nonwoven material. In one embodiment, the outer cover layer 42 may comprise a film, a foam, a nonwoven, a woven material, or the like and/or combinations thereof such as a laminate of a film and a nonwoven.

In one embodiment, the belt 40 may be at least partially formed, or fully formed, when the front and rear belts 84 and 86 are permanently or refastenably connecting together to form the seams 32. Any suitable seams may be formed, as known to those of skill in the art. The belt 40 may be ring-like and elastic. The ring-like elastic belt 40 may extend about the waist opening 36 of the pant 20 and act to dynamically create fitment forces and to distribute the forces dynamically generated during wear.

Figure 29:
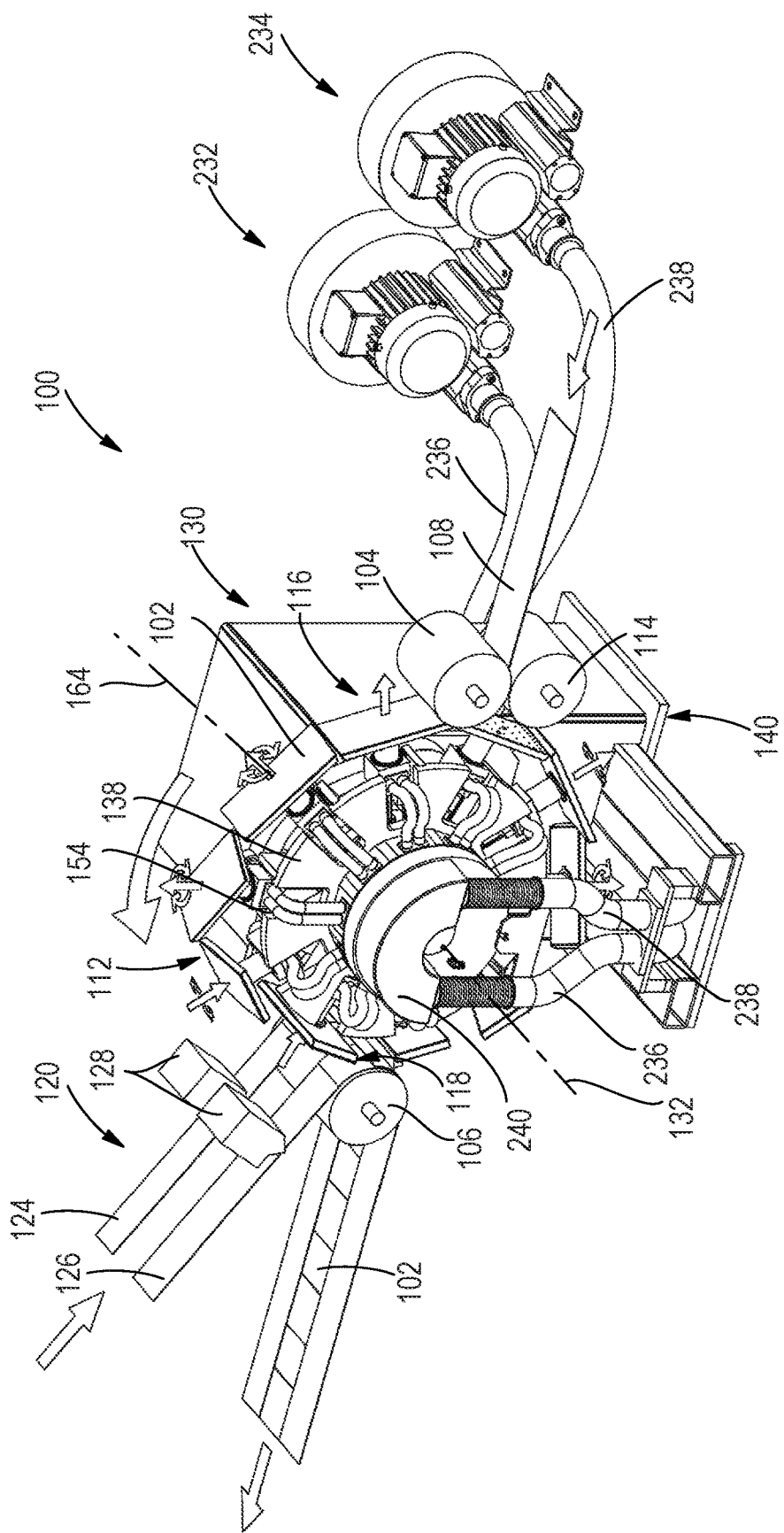
FIG. 29 is a front perspective view of a transfer assembly configured to transfer a discrete article from a first moving carrier member to a second moving carrier member.
Figure 30:
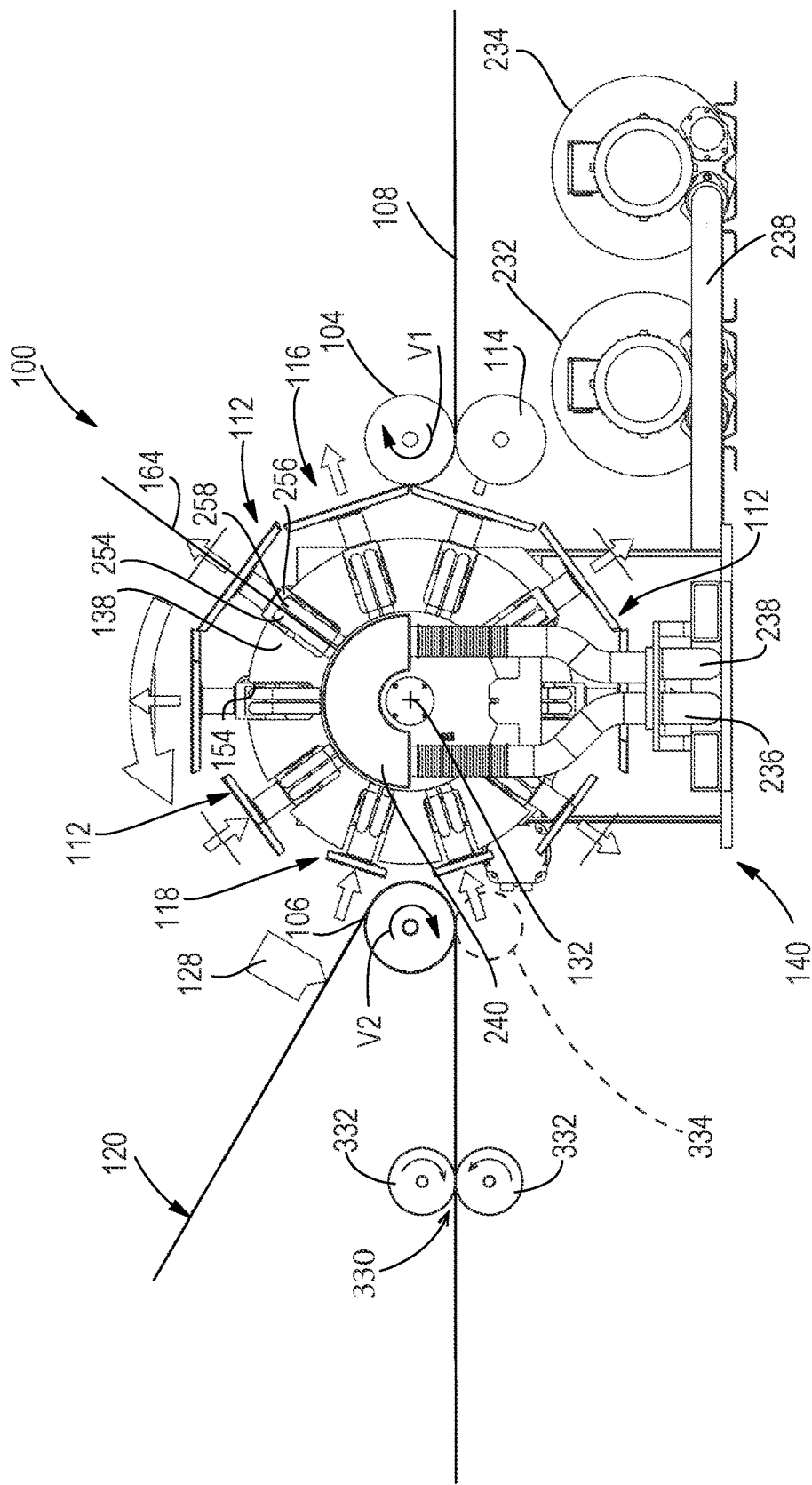
FIG. 30 is an elevation view of the transfer assembly shown in FIG. 29.
Figure 31:
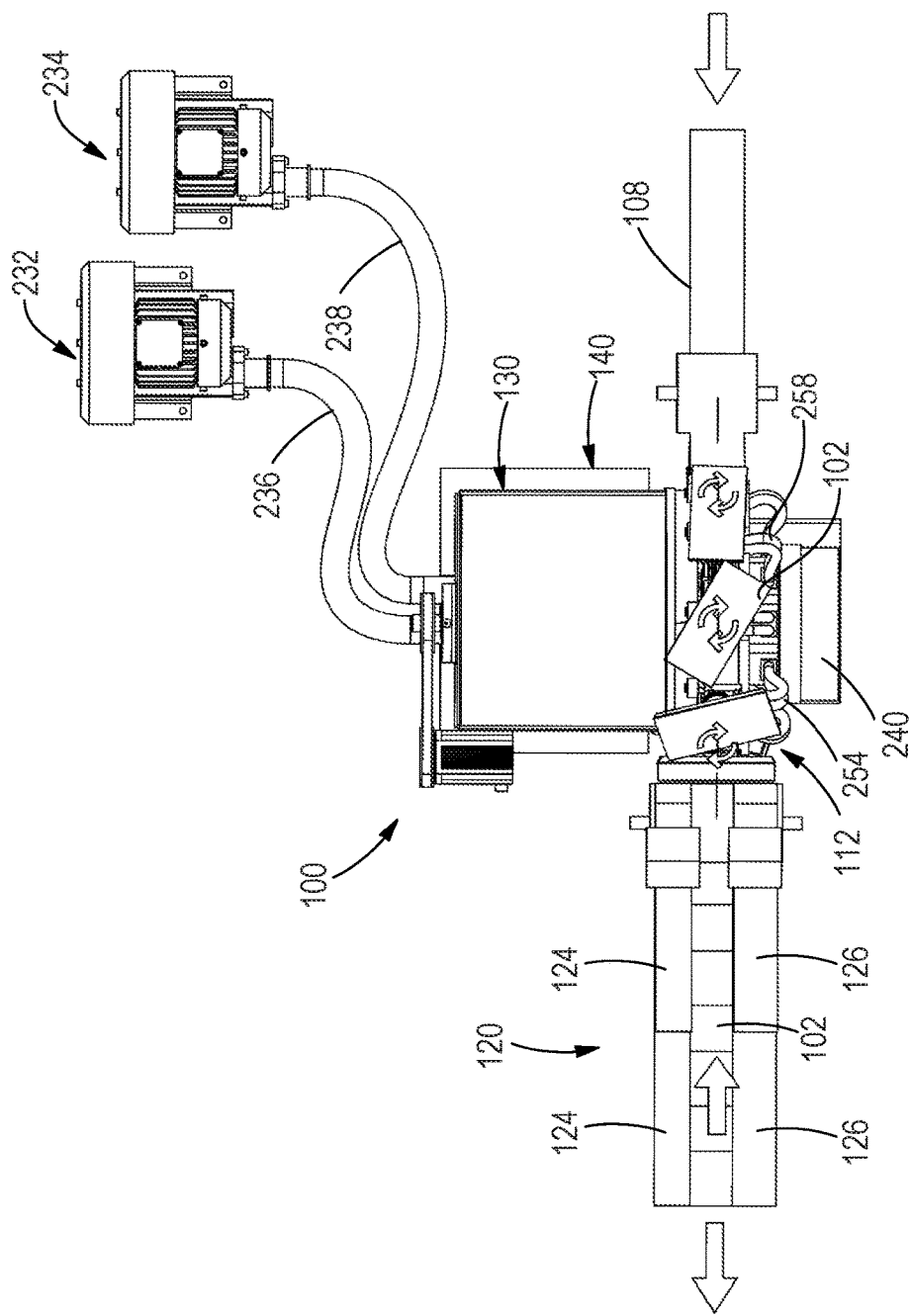
FIG. 31 is a top plan view of the transfer assembly shown in FIG. 29.
Figure 32:
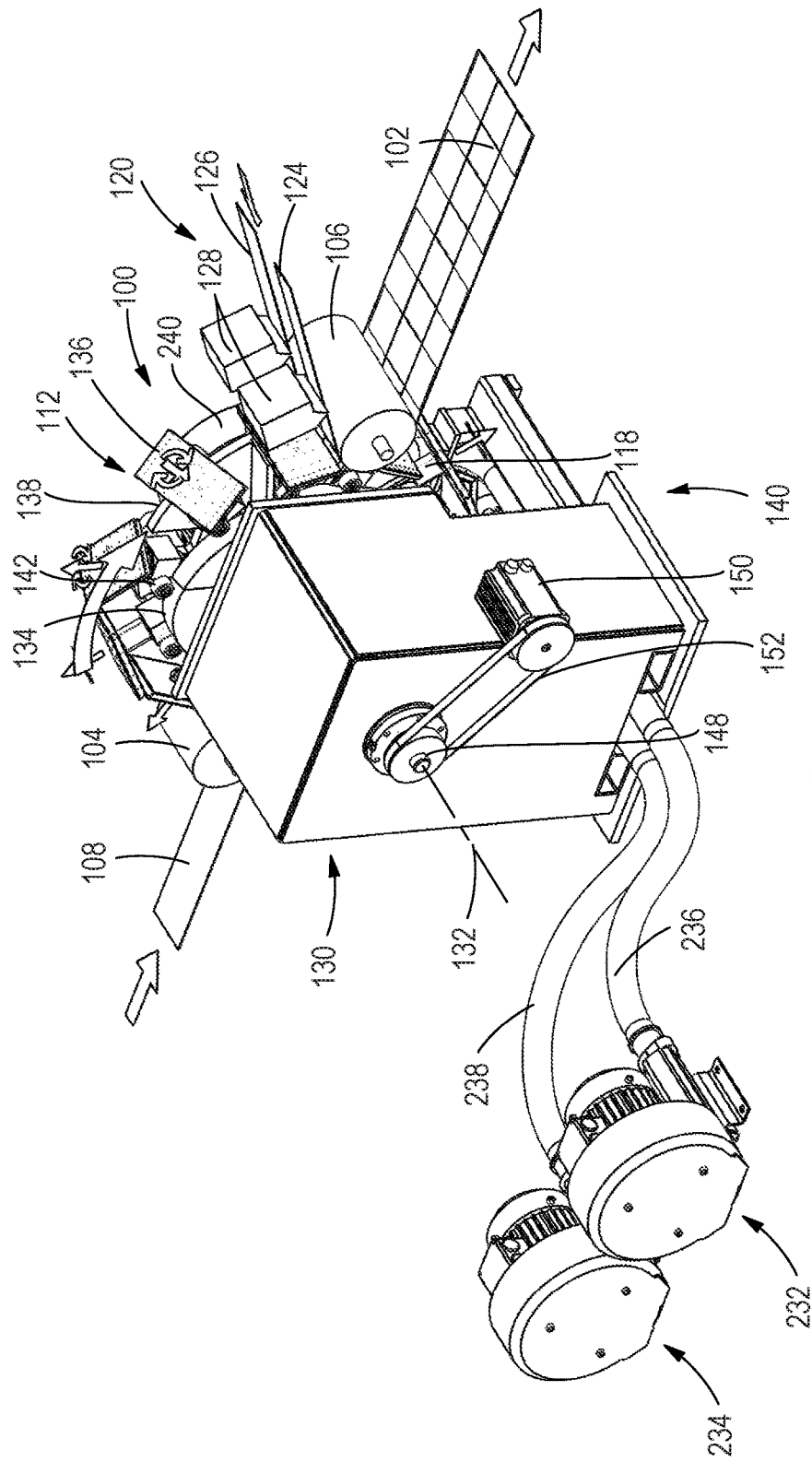
FIG. 32 is a rear perspective view of the transfer assembly shown in FIG. 29.

In one embodiment, referring to FIGS. 29-32, a transfer assembly 100 for transferring discrete articles from or to a moving carrier member is illustrated. FIG. 29 is a front perspective view of the transfer assembly 100. FIG. 30 is a front view of the transfer assembly 100. FIG. 31 is a top view of the transfer assembly 100. FIG. 32 is a rear perspective view of the transfer assembly 100. The transfer assembly 100 may transfer the discrete articles 102 from a first moving carrier member 104 to a second moving carrier member 106. The moving carrier members 104 and 106 from and to which the discrete articles 102 are transferred may be rolls, drums, curved conveyors, linear conveyors, and/or discrete heads following a curvilinear path, for example. The first and second moving carrier members 104 and 106 may be moving at a different surface velocity or at the same surface velocity. The transfer assembly 100 may pick up the discrete article 102 at a first velocity, V1, from the first moving carrier member 104 and may apply the discrete article 102 at a second velocity, V2, to the second moving carrier member 106. The first velocity, V1, and the second velocity, V2, at the point or zone of discrete article transfer to and from the first and second moving carrier members 104 and 106 may be tangential or linear velocities.

In one embodiment, a continuous web of articles 108 may be fed on a roll or other conveying mechanism toward the first moving carrier member 104. Once a portion of the web of discrete articles 108 long enough to form a discrete article 102 is engaged with the first moving carrier member 104 and/or is engaged with a portion of a transfer member 112 of the transfer assembly 100, a knife integral to the first moving carrier member 104 may cut the web 108 into discrete articles 102 against an anvil roll 114. The knife may be a flex knife, a die cutter, a shear knife, or any other suitable knife or cutting device or mechanism. Knife and anvil roll technology is generally known in the art. In other embodiments, previously cut discrete articles 102 may be fed on the conveyor toward the first moving carrier member 104.

Portions of the transfer members 112 of the present disclosure may also turn between a first position 116 and at least a second position 118 when transferring the discrete articles 102 between the first and second moving carrier members 104 and 106. As a result, the discrete articles 102 may be turned between a first position 116 and a second position 118. The portions of the transfer members 112 may be turned using rotation assemblies engaged with a portion of each transfer member 112, as described in further detail below. The discrete articles 102 may be turned between 30 and 180 degrees, between 40 and 150 degrees, between 60 and 120 degrees, between 75 and 105 degrees, 45 degrees, about 90 degrees (e.g., +/−5 degrees), 90 degrees, and 180 degrees, specifically reciting each degree within the above-recited ranges. Optionally, the discrete articles 102 may also not be turned at all and the transfer assembly may be used for conveying and/or repitching the discrete articles 102 without turning them.

Again referring to FIGS. 29-32, continuous webs of components 120 may be moving towards, over, and away from the second moving carrier member 106 on a roller, conveyor, or other mechanism. In one example, these webs of components 120 may be front belts 124 and rear belts 126, although in other embodiments, the webs of components 120 may be various other components or even discrete components that have been previously cut from a continuous web. An adhesive may be applied to the webs of components 120 or discrete components using adhesive dispensers 128. The adhesive dispensers 128 are optional and are used to illustrate one example use of the transfer assemblies 100 of the present disclosure. The adhesive may be applied to portions of the webs of components 120 prior to those portions being moved over the second moving carrier member 106. As a result, a discrete article 102 being transferred to the second moving carrier member 106 may be adhesively attached to the webs of components 120 when transferred onto the second moving carrier member 106. In one example, the discrete article 102 may be a chassis 38 and the front waist panel 52 of the chassis 38 may be adhesively attached to the continuous web of front belts 124 and the rear waist panel 54 of the chassis 38 may be adhesively attached to the continuous web of rear belts 126. This may form a web of absorbent articles 10. The web of absorbent articles 10 may then be cut or separated into discrete absorbent articles 10, such as the absorbent article of FIG. 27.

EXAMPLES

A. A method for transferring and/or moving multiple different discrete articles on a manufacturing line, the method comprising the steps of:
  a. providing a transfer member comprising a transfer surface, the transfer surface comprising:
    i. a first zone comprising a first plurality of fluid ports and being configured to accept a first discrete article; and
    ii. a second zone substantially surrounding the first zone, the second zone comprising a second plurality of fluid ports, wherein the first zone and the second zone collectively are configured to accept a second discrete article that is different in size and/or shape from the first discrete article;
  b. applying fluid pressure only to the first plurality of fluid ports while contacting the first discrete article with the transfer surface; and
  c. separately from step (b), applying fluid pressure to both the first plurality of fluid ports and the second plurality of fluid ports while contacting the second discrete article with the transfer surface;
  d. wherein the each of the first discrete article and the second discrete article is a disposable absorbent article or component thereof B. The method according to Paragraph A, wherein the first discrete article has a different size from the second discrete article.

C. The method according to Paragraph A, wherein the first discrete article has a different shape than the second discrete article.

D. The method according to Paragraph A, wherein the first discrete article has both a different size and a different shape than the second discrete article.

E. The method according to any one of Paragraphs A-D, wherein the transfer surface comprises (iii) a third zone proximate the second zone, the third zone comprising a third plurality of fluid ports, and wherein at least two of the first zone, the second zone, and the third zone are configured to accept a third discrete article that is different from the first discrete article and the second discrete article.

F. The method according to Paragraph E, wherein the third zone substantially surrounds the second zone on multiple sides thereof.

G. The method according to Paragraph E, wherein the third zone is disposed on only one side of the second zone.

H. The method according to any one of Paragraphs A-G, wherein the transfer surface is substantially flat.

I. The method according to any one of Paragraphs A-H, wherein during step (b) and/or step (c) the transfer surface is rotated.

J. The method according to any one of Paragraphs A-I, wherein during step (b) and/or step (c) the transfer surface is both translated and rotated.

K. The method according to any one of Paragraphs A-J, wherein during step (b) and/or step (c) the transfer surface is both rotated about a first axis and rotated about a second axis.

L. The method according to any one of Paragraphs A-K, wherein fluid pressure applied to the first plurality of fluid ports is independently supplied from fluid pressure applied to the second plurality of fluid ports.

M. The method according to any one of Paragraphs A-L, comprising the step of (e) orbiting the transfer member through a pick-up zone supplying a plurality of first discrete articles and a drop-off zone to deliver the plurality of first discrete articles.

N. A method for transfer and/or moving multiple discrete articles on a manufacturing line, the method comprising the steps of:
  a. providing a transfer member comprising a fluid pressure chamber comprising a wall; the wall comprising an inner surface, an outer surface, a first plurality of fluid ports extending from an inlet on the inner surface to an outlet on the outer surface, and a second plurality of fluid ports extending from an inlet on the inner surface to an outlet on the outer surface;

b. applying fluid pressure to the fluid pressure chamber;
c. communicating fluid pressure to the first plurality of fluid ports while impeding fluid pressure to at least some of the second plurality of fluid ports to hold a first discrete article on the outer surface; and
d. separately from step (c), communicating fluid pressure to both the first plurality of fluid ports and the second plurality of fluid ports to hold a second discrete article on the outer surface;
e. wherein the second discrete article is different in size and/or shape from the first discrete article; and
f. wherein the each of the first discrete article and the second discrete article is a disposable absorbent article or component thereof O. The method according to Paragraph N, wherein during step (c) the inlet of at some of the second plurality of fluid ports is masked.

P. The method according to Paragraph N or O, wherein during step (c) the outlet of at some of the second plurality of fluid ports is masked.

Q. The method according to any one of Paragraphs N-P, wherein during step (c) fluid pressure is completely blocked from being communicated to the second plurality of fluid ports.

R. The method according to any one of Paragraphs N-Q, wherein the first discrete article has a different size from the second discrete article.

S. The method according to any one of Paragraphs N-R, wherein the first discrete article has a different shape than the second discrete article.

T. The method according to any one of Paragraphs N-S, wherein the first discrete article has both a different size and a different shape than the second discrete article.

U. The method according to any one of Paragraphs N-T, wherein some of the first plurality of fluid ports are situated on one side of the second plurality of fluid ports and others of the first plurality of fluid ports are situated on an opposite side of the second plurality of fluid ports.

V. The method according to any one of Paragraphs N-U, wherein the first plurality of fluid ports are situated only on one side of the second plurality of fluid ports.

W. A method for transfer and/or moving multiple discrete articles on a manufacturing line, the method comprising the steps of:
a. providing a transfer member comprising a fluid pressure chamber comprising a wall; the wall comprising an inner surface, an outer surface, a first plurality of fluid ports extending from an inlet on the inner surface to an outlet on the outer surface, and a second plurality of fluid ports extending from an inlet on the inner surface to an outlet on the outer surface;
b. providing a stem extending from the transfer member and comprising a first fluid conduit to the fluid pressure chamber and a second fluid conduit to the fluid pressure chamber;
c. providing a fluid restrictor associated with the stem, the fluid restrictor being moveable from a first position to a second position;
d. communicating fluid pressure to the stem;
e. positioning the fluid restrictor to the first position so that fluid pressure is communicated only to the first plurality of fluid ports via the first fluid conduit to hold a first discrete article on the outer surface; and
f. separately from step (e), positioning the fluid restrictor to the second position so that fluid pressure is communicated to both the first plurality of fluid ports via the first fluid conduit and the second plurality of fluid ports via the second fluid conduit to hold a second discrete article on the outer surface;
g. wherein the second discrete article is different in size and/or shape from the first discrete article; and
h. wherein the each of the first discrete article and the second discrete article is a disposable absorbent article or component thereof X. The method according to Paragraph W, wherein the first discrete article has a different size from the second discrete article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for applying fluid pressure to a transfer member configured to transfer multiple discrete articles, the method comprising the steps of:
a. providing a transfer member comprising a transfer surface, the transfer surface comprising:
  i. a first zone comprising a first plurality of fluid ports and being configured to accept a first discrete article; and
  ii. a second zone at least partially surrounding the first zone, the second zone comprising a second plurality of fluid ports, wherein the first zone and the second zone collectively are configured to accept a second discrete article that is different in size and/or shape from the first discrete article;
b. applying fluid pressure only to the first plurality of fluid ports while contacting the first discrete article with the transfer surface; and
c. separately from step (b), applying fluid pressure to both the first plurality of fluid ports and the second plurality of fluid ports while contacting the second discrete article with the transfer surface;
d. wherein each of the first discrete article and the second discrete article is a disposable absorbent article or component thereof.

2. The method of claim 1, wherein the first discrete article has a different size from the second discrete article.

3. The method of claim 1, wherein the first discrete article has a different shape than the second discrete article.

4. The method of claim 1, wherein the first discrete article has both a different size and a different shape than the second discrete article.

5. The method of claim 1, wherein the transfer surface comprises (iii) a third zone proximate the second zone, the third zone comprising a third plurality of fluid ports, and wherein at least two of the first zone, the second zone, and the third zone are configured to accept a third discrete article that is different from the first discrete article and the second discrete article.

6. The method of claim 5, wherein the third zone substantially surrounds the second zone on multiple sides thereof.

7. The method of claim 5, wherein the third zone is disposed on only one side of the second zone.

8. The method of claim 1, wherein the transfer surface is substantially flat.

9. The method of claim 1, comprising rotating the transfer surface during step (b) and/or step (c).

10. The method of claim 1, comprising translating and rotating the transfer surface during step (b) and/or step (c).

11. The method of claim 1, comprising rotating the transfer surface about a first axis and about a second axis during step (b) and/or step (c).

12. The method of claim 1, comprising independently supplying fluid pressure to the first plurality of fluid ports and to the second plurality of fluid ports.

13. The method of claim 1, comprising the step of (e) orbiting the transfer member through a pick-up zone supplying a plurality of first discrete articles and a drop-off zone to deliver the plurality of first discrete articles.

14. A method for applying fluid pressure to a transfer member configured to transfer multiple discrete articles, the method comprising the steps of:
    a. providing a transfer member comprising a transfer surface, the transfer surface comprising:
        i. a first zone comprising a first plurality of fluid ports and being configured to accept a first discrete article; and
        ii. a second zone on one side of the first zone, the second zone comprising a second plurality of fluid ports, wherein the first zone and the second zone collectively are configured to accept a second discrete article that is different in size and/or shape from the first discrete article;
    b. applying fluid pressure only to the first plurality of fluid ports while contacting the first discrete article with the transfer surface; and
    c. separately from step (b), applying fluid pressure to both the first plurality of fluid ports and the second plurality of fluid ports while contacting the second discrete article with the transfer surface;
    d. wherein each of the first discrete article and the second discrete article is a disposable absorbent article or component thereof.

15. The method of claim 14, wherein the first discrete article has a different size from the second discrete article.

16. The method of claim 14, wherein the transfer surface comprises (iii) a third zone on another side of the first zone, the third zone comprising a third plurality of fluid ports, and wherein the first zone, the second zone, and the third zone are configured to accept a third discrete article that is different in size and/or shape from the first discrete article and the second discrete article.

17. The method of claim 14, wherein the transfer surface is substantially flat.

18. The method of claim 14, comprising rotating the transfer surface during step (b) and/or step (c).

19. The method of claim 14, comprising translating and rotating the transfer surface during step (b) and/or step (c).

20. A method for applying fluid pressure to a transfer member configured to transfer multiple discrete articles, the method comprising the steps of:
    a. providing a transfer member comprising a transfer surface, the transfer surface comprising:
        i. a first zone comprising a first plurality of fluid ports and being configured to accept a first discrete article; and
        ii. a second zone comprising a second plurality of fluid ports, wherein the first zone and the second zone collectively are configured to accept a second discrete article that is different in size and/or shape from the first discrete article;
    b. applying fluid pressure only to the first plurality of fluid ports while contacting the first discrete article with the transfer surface; and
    c. separately from step (b), applying fluid pressure to both the first plurality of fluid ports and the second plurality of fluid ports while contacting the second discrete article with the transfer surface;
    d. wherein each of the first discrete article and the second discrete article is a disposable absorbent article or component thereof.

\* \* \* \* \*